US012805479B2

(12) United States Patent
Holland et al.

(10) Patent No.: US 12,805,479 B2
(45) Date of Patent: Nov. 24, 2026

(54) **METHODS OF INCREASING YIELD OF *Prunus dulcis* AND PLANTS PRODUCED THEREBY**

(71) Applicant: The State of Israel, Ministry of Agriculture & Rural Development, Agricultural Research Organization (ARO) (Volcani Institute), Rishon-LeZion (IL)

(72) Inventors: Doron Holland, HaSolelim (IL); Irit Bar-Yaakov, Qiryat Tivon (IL); Rotem Harel-Beja, Misgav (IL); Hillel Brukental, Harish (IL); Tamar Shemer (Azoulay), Kfar Yona (IL); Kamel Hatib, Arraba (IL)

(73) Assignee: The State of Israel, Ministry of Agriculture & Rural Development, Agricultural Research Organization (ARO) (Volcani Institute), Rishon-LeZion (IL)

( * ) Notice: Subject to any disclaimer, the term of this patent is extended or adjusted under 35 U.S.C. 154(b) by 597 days.

(21) Appl. No.: 17/885,638

(22) Filed: Aug. 11, 2022

(65) Prior Publication Data

US 2023/0061359 A1 Mar. 2, 2023

Related U.S. Application Data

(60) Provisional application No. 63/232,237, filed on Aug. 12, 2021.

(51) Int. Cl.

*A01H 6/74* (2018.01)
*C12N 15/82* (2006.01)

(52) U.S. Cl.

CPC ....... *A01H 6/7427* (2018.05); *C12N 15/8201* (2013.01); *C12N 15/8243* (2013.01); *C12N 15/8261* (2013.01)

(58) Field of Classification Search

None

See application file for complete search history.

(56) References Cited

U.S. PATENT DOCUMENTS

2016/0201076 A1 7/2016 Ge et al.

FOREIGN PATENT DOCUMENTS

| | | |
|---|---|---|
| ES | 2940627 | 5/2023 |
| WO | WO 01/49104 | 7/2001 |

OTHER PUBLICATIONS

Trainin T, Brukental H, Shapira O, Attia Z, Tiwari V, Hatib K, Gal S, Zemach H, Belausov E, Charuvi D, Holland D, Azoulay-Shemer T. Physiological characterization of the wild almond *Prunus arabica* stem photosynthetic capability. Front Plant Sci. Jul. 29, 2022;13: 941504, pp. 1-22. (Year: 2022).*

(Continued)

*Primary Examiner* — Amjad Abraham
*Assistant Examiner* — Dequantarius Javon Speed

(57) ABSTRACT

A method of increasing yield of a domesticated *Prunus dulcis* plant is provided. Also provided is a method of increasing stem photosynthetic capability (SPC) and a method of identifying a donor plant for use in a breeding program of *Prunus dulcis*. Provided are domesticated *Prunus dulcis* with enhanced agricultural traits.

4 Claims, 9 Drawing Sheets

Figure 1:
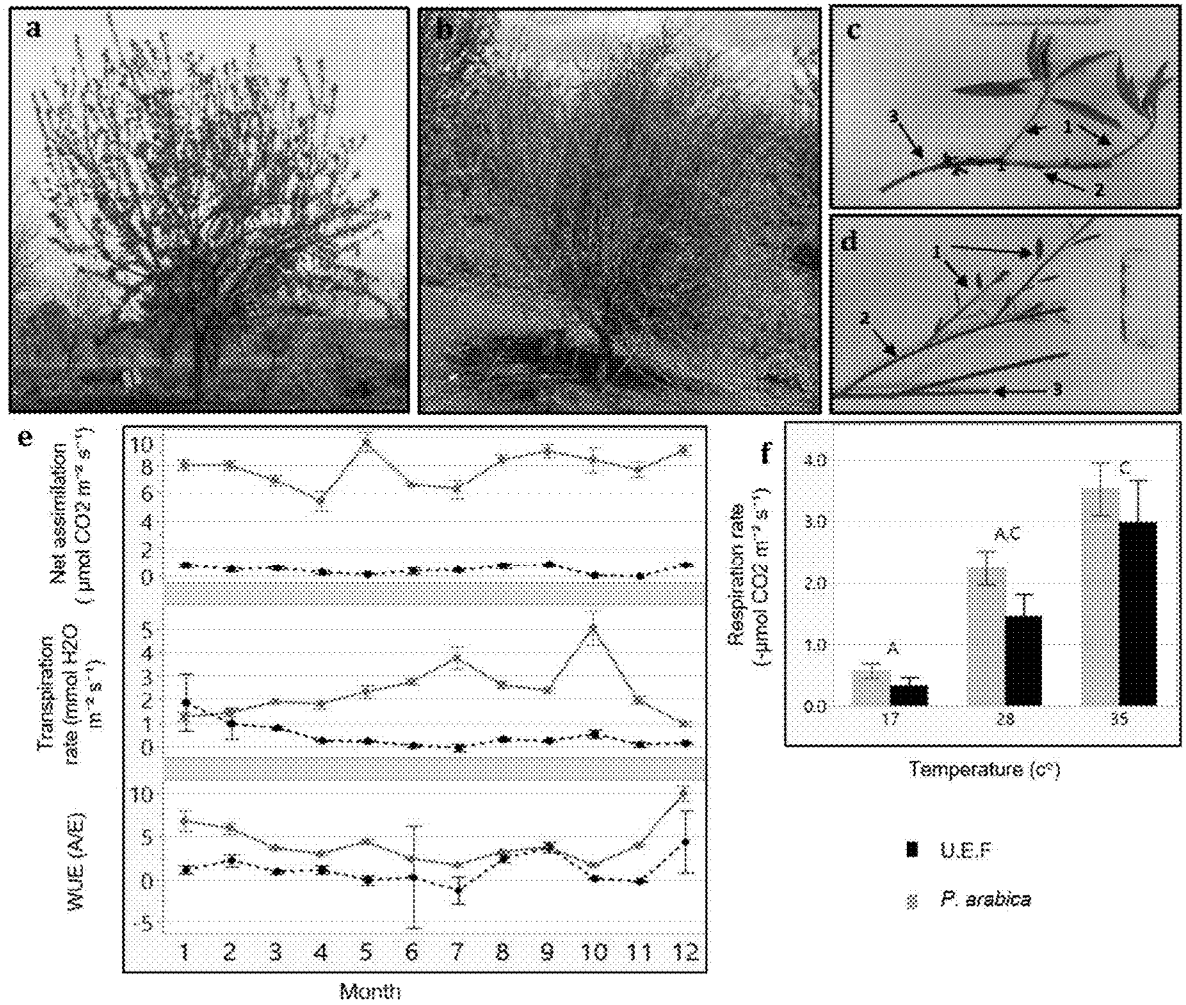

Specification includes a Sequence Listing.

(56) References Cited

OTHER PUBLICATIONS

Gonzalo, M.J., Dirlewanger, E., Moreno, M.Á. et al. Genetic analysis of iron chlorosis tolerance in Prunus rootstocks. Tree Genetics & Genomes 8, 943-955 (2012). (Year: 2012).*
Diamond, M. I., Miner, J. N., Yoshinaga, S. K., & Yamamoto, K. R. (1990). Transcription factor interactions: selectors of positive or negative regulation from a single DNA element. Science, 249(4974), 1266-1272. (Year: 1990).*
Martínez, M. L., Penci, M. C., Marin, M. A., Ribotta, P. D., & Maestri, D. M. (2013). Screw press extraction of almond (*Prunus dulcis* (Miller) DA Webb): Oil recovery and oxidative stability. Journal of Food Engineering, 119(1), 40-45. (Year: 2013).*
Girma, A., Skidmore, A. K., De Bie, C. A. J. M., & Bongers, F. (2015). Understanding *Boswellia papyrifera* tree secondary metabolites through bark spectral analysis. ISPRS Journal of Photogrammetry and Remote Sensing, 105, 30-37. (Year: 2015).*
Sorkheh, K., Shiran, B., Rouhi, V. et al. Phenotypic diversity within native Iranian almond (*Prunus* spp.) species and their breeding potential. Genet Resour Crop Evol 56, 947-961 (2009). https://doi.org/10.1007/s10722-009-9413-7 (Year: 2009).*
Examination Report Dated Jun. 18, 2024 From the Spanish Patent Office Re. Application No. 202230747 and Its Translation Into English. (9 pages).
Brukental et al. "Revealing the Genetic Components Responsible for the Unique Photosynthetic Stem Capability of the Wild Almond *Prunus arabica* (Olivier) Meikle", Frontiers in Plant Science, 12, Article No. 779970: 1-14, Nov. 25, 2021.
Guo Chunmiao et al. "Developmental Transcriptome Profiling Uncovered Carbon Signaling Genes Associated with Almond Fruit Drop", Scientific Reports, 11: 3401, 1-12, Feb. 9, 2021.
Resultado de Examen [Examination Report] Dated Aug. 19, 2025 From the Ministerio de Industria y Turismo, Oficina Española de Patentes y Marcas [Spanish Patent Office] Rc. Application No. 202230747 and Its Translation Into English. (8 Pages).

* cited by examiner

Figures 1A-F

Figures 2A-D

Figures 6A-C
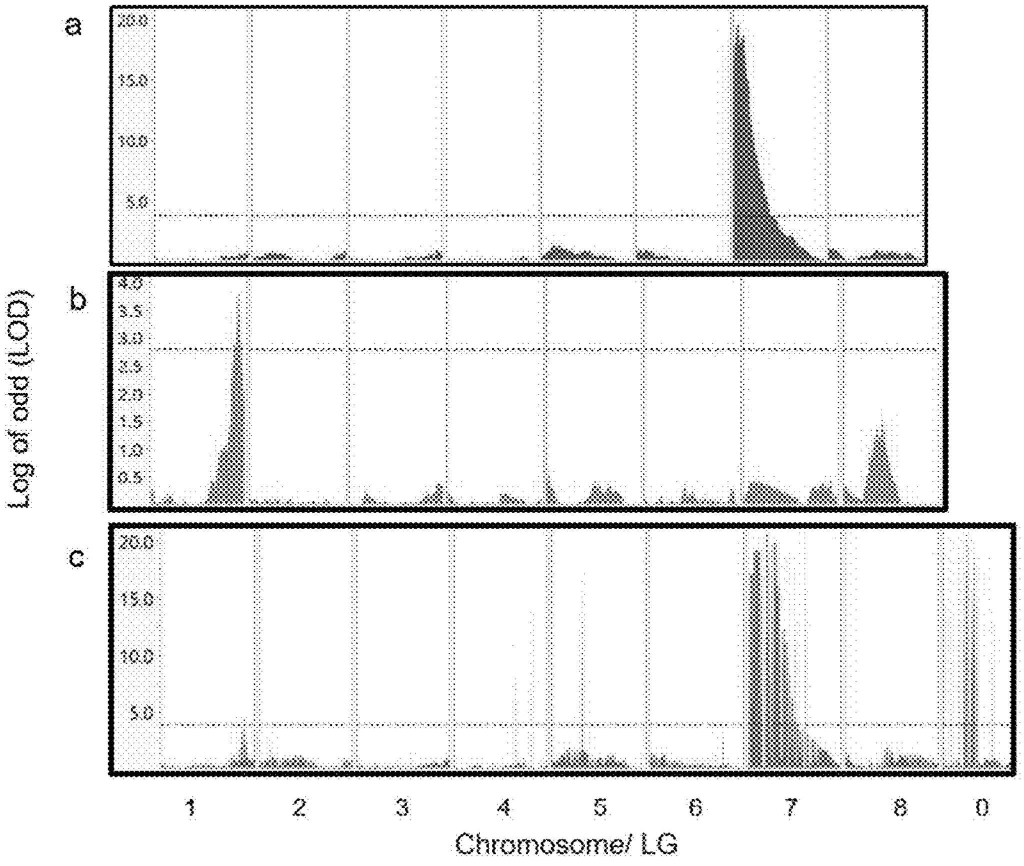

Figures 7A-C
a
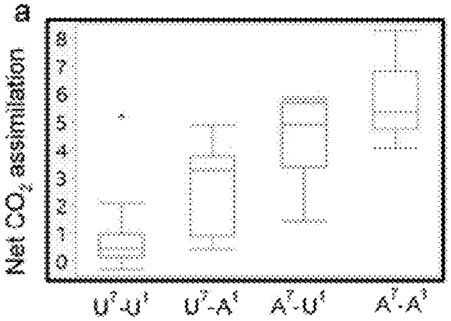
b
| Allelic state | | Least Sq Mean (net $CO_2$ assimilation) | SE |
|---|---|---|---|
| Locus 7 (chr 7) | Locus 1 (chr 1) | | |
| A | A | [a]5.7339041 | 0.250632 |
| A | U | [b]4.4461958 | 0.389623 |
| U | A | [c]1.827375 | 0.318128 |
| U | U | [c]0.8019354 | 0.275505 |
c
Effect Summary
| Source | LogWorth | PValue |
|---|---|---|
| LOCUS 7 | 18.877 | 0.00000 |
| LOCUS 1 | 3.389 | 0.00041 |
| LOCUS 1*LOCUS 7 | 0.170 | 0.67633 |

Fig. 8: *AGL 82* protein modification in *P. arabica* and U.E.F.

a

P. arabica del 21 SEQ ID NO: 4 GATGTTTGCTTGATCGTCTATGAAGCCGATCA---------------------ACCGGAGACGTGGCCGCGGGATCCAAATCA P. arabica del 17 SEQ ID NO: 5 GATGTTTGCTTGATCGTCTATGAAGCCGATCAA-----------------TCAACCGGAGACGTGGCCGCGGGATCCAAATCA U.E.F SEQ ID NO: 6 GATGTTTGCTTGATCGTCTATGAAGCCGATCAAAAGAAGGGGAGGGCAGTTCAACCGGAGACGTGGCCGCGGGATCCAAATCA b

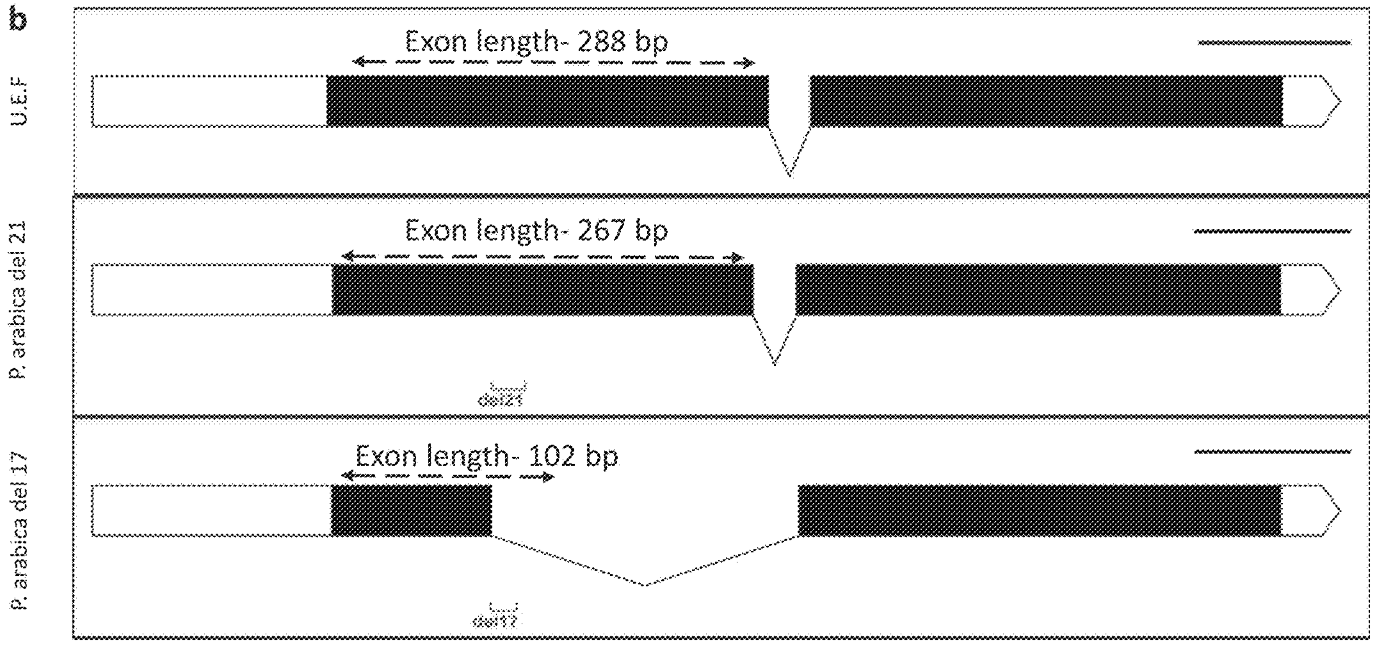

a
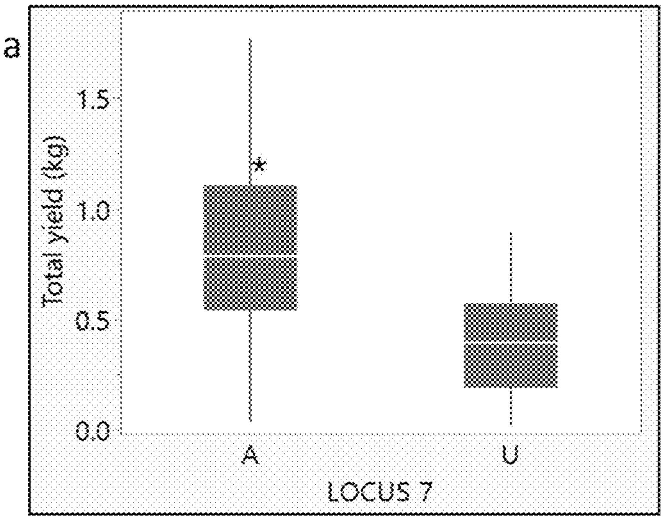
b
Least Squares Means Table
| Level | Least Sq Mean | Std Error |
|---|---|---|
| A | 0.84768571 | 0.07151859 |
| U | 0.46354286 | 0.07151859 |
Figures 9A-B

SEQUENCE LISTING

```
Sequence total quantity: 20
SEQ ID NO: 1           moltype = DNA  length = 813
FEATURE                Location/Qualifiers
misc_feature           1..813
                       note = P.arabica_Del17 nucleic acid sequence
source                 1..813
                       mol_type = other DNA
                       organism = synthetic construct
SEQUENCE: 1
agatccagtt agatcgctgc aatatattat tttcttgggt tcttctaatc taaacatcaa  60
aatttttgtc tctgtgtttt gtggaattat agaagatatg gtggctcctc gaagaagctg  120
cttagaactc atacctaatg agggcactcg gaagatgaca tttcggaagc gaaagaagag  180
tatatataaa aaggccgacg agctttcgaa gctttgtggt attgatgttt gcttgatcgt  240
ctatgaagcc gatcaatcaa ccggagacgt ggccgcggga tccaaatcaa ttcaaacgca  300
ttctcaacaa gtacaaggat tctaaggata cgtccacacc cagattgaaa agaaacttta  360
ttatgtctga tttttatgag gacaagaaag atcacgtgga tgaggatgac gaaaagtttc  420
aaaattcagg gaagaagatt tttgagggga atacccgaca aagtttcaaa atttagggaa  480
gaagatttct gaggaggagt acccgagatg ggacgatcga atagatgatt tttcgcagga  540
cgaattgact gagctcattg cttcactcga atccaagata caagttgcaa ccaagaagat  600
tgattctatg gaaagatata tggggtttgc taagaaacaa aatcaaagtt tggtccggga  660
agagattaat catgatgagc agccctatca agtccctgct ttgatgtctc ctccatcact  720
tgtgcattgt ccaatgttgc caagtgcatg ggtttcaagc tcagaatcgg tgaagagcta  780
atcagaactt gacaacctgt gtatctaatc ctt                               813

SEQ ID NO: 2           moltype = DNA  length = 809
FEATURE                Location/Qualifiers
misc_feature           1..809
                       note = P.arabica_Del21 nucleic acid sequence
source                 1..809
                       mol_type = other DNA
                       organism = synthetic construct
SEQUENCE: 2
agatccagtt agatcgctgc aatatattat tttcttgggt tcttctaatc taaacatcaa  60
aatttttgtc tctgtgtttt gtggaattat agaagatatg gtggctcctc gaagaagctg  120
cttagaactc atacctaatg agggcactcg gaagatgaca tttcggaagc gaaagaagag  180
tatatataaa aaggccgacg agctttcgaa gctttgtggt attgatgttt gcttgatcgt  240
ctatgaagcc gatcaaccgg agacgtggcc gcgggatcca aatcaattca aacgcattct  300
caacaagtac aaggattcta aggatacgtc cacacccaga ttgaaaagaa actttattat  360
gtctgatttt tatgaggaca agaaagatca cgtggatgag gatgacgaaa agtttcaaaa  420
ttcagggaag aagatttttg aggggaatac ccgacaaagt ttcaaaattt agggaagaag  480
atttctgagg aggagtaccc gagatgggac gatcgaatag atgatttttc gcaggacgaa  540
ttgactgagc tcattgcttc actcgaatcc aagatacaag ttgcaaccaa gaagattgat  600
tctatggaaa gatatatggg gtttgctaag aaacaaaatc aaagtttggt ccgggaagag  660
attaatcatg atgagcagcc ctatcaagtc cctgctttga tgtctcctcc atcacttgtg  720
cattgtccaa tgttgccaag tgcatgggtt tcaagctcag aatcggtgaa gagctaatca  780
gaacttgaca acctgtgtat ctaatcctt                                    809

SEQ ID NO: 3           moltype = DNA  length = 830
FEATURE                Location/Qualifiers
misc_feature           1..830
                       note = Prunus dulcis U.E.F nucleic acid sequence
source                 1..830
                       mol_type = other DNA
                       organism = synthetic construct
SEQUENCE: 3
agatccaatt agatctctgc aatatattat tttcttgggt tcttctaatc taaacatcaa  60
aatttttgtc tctctgtttt gtggaattat agaagatatg gtggctcctc gaagaagcag  120
cttagaactc atacctaatg agagcactcg gaagatgaca tttcggaagc gaaagaagag  180
tatatataaa aaggccgacg agctttcgaa gctttgtggt attgatgttt gcttgatcgt  240
ctatgaagcc gatcaaaaga aggggagggc agttcaaccg gagacgtggc cgcgggatcc  300
aaatcaattc aaacgcattc tcaacaagta caaggattct aaggatacgt ccacacccag  360
attgaaaaga aactttatta tgtctgattt ttatgaggtc aagaaagatc acgtggatga  420
ggatgacgaa aagtttcaaa attcagggaa gaagattttt gaggggaata cccgacaaag  480
tttcaaaatt tagggaagaa gatttctgag gaggagtacc cgagatggga cgatcgaata  540
gatgattttt cgcaggacga attgactgag ctcattgctt cactcgaatc caagatacat  600
```

```
gttgcaacca agaagattga ttctatggaa agatatatgg ggtttgctaa gaaacaaaat  660
caaagtttgg tctgggaaga gattaatcat gatgagcagc cctatcaagt ccctgctttg  720
atgtctcctc catcacttgt gcattgtcca atgttgccaa gtgcatgggt ttcaagctca  780
gaatcggtga agagctaatc agaacttgac aacctgtgta tctaatcctt             830

SEQ ID NO: 4           moltype = DNA  length = 62
FEATURE                Location/Qualifiers
misc_feature           1..62
                       note = partial sequence of seq ID number 2 ( for alignment)
source                 1..62
                       mol_type = other DNA
                       organism = synthetic construct
SEQUENCE: 4
gatgtttgct tgatcgtcta tgaagccgat caaccggaga cgtggccgcg ggatccaaat  60
ca                                                                 62

SEQ ID NO: 5           moltype = DNA  length = 66
FEATURE                Location/Qualifiers
misc_feature           1..66
                       note = partial sequence of seq ID number 1 ( for alignment)
source                 1..66
                       mol_type = other DNA
                       organism = synthetic construct
SEQUENCE: 5
gatgtttgct tgatcgtcta tgaagccgat caatcaaccg gagacgtggc cgcgggatcc  60
aaatca                                                             66

SEQ ID NO: 6           moltype = DNA  length = 83
FEATURE                Location/Qualifiers
misc_feature           1..83
                       note = partial sequence of seq ID number 3 ( for alignment)
source                 1..83
                       mol_type = other DNA
                       organism = synthetic construct
SEQUENCE: 6
gatgtttgct tgatcgtcta tgaagccgat caaaagaagg ggagggcagt tcaaccggag  60
acgtggccgc gggatccaaa tca                                          83

SEQ ID NO: 7           moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 7
cagttgaaat gcccggtttt gacaaatgca ggagcctgag                        40

SEQ ID NO: 8           moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 8
aaggtttatg atgactatat attgaaaatt tgtttacttg                        40

SEQ ID NO: 9           moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 9
gttcaactgt tagctttact gttctcatgt tgtaggtttg                        40

SEQ ID NO: 10          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 10
ctgcagtata aagaaacaag tgaccagcat atgatttgaa                        40

SEQ ID NO: 11          moltype = DNA  length = 40
```

-continued

```
FEATURE                Location/Qualifiers
misc_feature           1..40
                       note = Single strand DNA oligonucleotide
source                 1..40
                       mol_type = other DNA
                       organism = synthetic construct
SEQUENCE: 11
gttcgcttct cccagataaa ccatctgcca tcgtcacttc                        40

SEQ ID NO: 12          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 12
taactataaa tatttcgtgg tcattttctt atctgtgttg                        40

SEQ ID NO: 13          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 13
ttacaaccct ataatgaaag atataatgat gggtatagtg                        40

SEQ ID NO: 14          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 14
catggtggac atccaagggg gagtgttgta actttcaagg                        40

SEQ ID NO: 15          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 15
cttgacatat gaaaatttgt tgtttatctg tgctaagttc                        40

SEQ ID NO: 16          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 16
acagatattc tgtccttgca acgtctgcac accaacaagc                        40

SEQ ID NO: 17          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 17
cccaagattt gtacgtgatg cttcagtgcc aactgataat                        40

SEQ ID NO: 18          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 18
aagggtagct aatttgaaga atgggtcaat gagctgccta                        40
```

-continued

```
SEQ ID NO: 19          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 19
cgaacaagat acggcatgac cactgaaaaa gatttgattt                   40

SEQ ID NO: 20          moltype = DNA  length = 40
FEATURE                Location/Qualifiers
misc_feature           1..40
                       note = Single strand DNA oligonucleotide
source                 1..40
                       mol_type = other DNA
                       organism = synthetic construct
SEQUENCE: 20
cctaaataaa gggggagaac aaggatttct tgctttgata                   40
```

METHODS OF INCREASING YIELD OF *Prunus dulcis* AND PLANTS PRODUCED THEREBY

RELATED APPLICATION

This application claims the benefit of priority under 35 USC § 119(e) of U.S. Provisional Patent Application No. 63/232,237 filed on Aug. 12, 2021, the contents of which are incorporated by reference as if fully set forth herein in their entirety.

SEQUENCE LISTING STATEMENT

The XML file, entitled 93587SequenceListing.xml, created on Aug. 11, 2022, comprising 29,391 bytes, submitted concurrently with the filing of this application is incorporated herein by reference.

FIELD AND BACKGROUND OF THE INVENTION

The present invention, in some embodiments thereof, relates to methods of increasing yield of *Prunus dulcis* and plants produced thereby.

Almond, *Prunus dulcis* (Mill.) D. A. Webb, is a major fruit tree crop worldwide. As a deciduous fruit tree, it enters dormancy during early winter and renews growth following the fulfillment of a variety-specific period of exposure to low temperatures, known as chilling requirements (CR) and adequate heat requirements. Exposure to a sufficient number of low winter-temperatures is essential for synchronized flowering in the early spring followed by efficient pollination, fruit set and fruit development[1]. CR limit growing areas of deciduous fruit trees and dramatically influence the yield and quality of fruit[2]. When winter temperature increases, CR are not sufficiently provided, and the metabolic activity increases[3]. As a result, carbohydrates are consumed, and intense starch synthesis occur. These changes lead to soluble carbohydrate (SC) deficiency in the buds during the period of flowering and fruit set, which results in disruptive flowering that may reduce yield[4-6]. The ability of the dormant almond to respond to this energy depletion is restricted, mainly due to the shortage in photosynthetic leaves during dormancy. Climate changing trends emphasize the urgent need for *Prunus dulcis* fruit crops to gain more plasticity for maintaining their nonstructural carbohydrate (NSC) reserves in warmer winters[2,7].

*P. Prunus arabica* (Olivier) Meikle, also known as *Amygdalus arabica* Olivier, defined as a different species from the domesticated almond *P. dulcis*. However, both belong to the *Prunus* genus and are a pail of the Rosacea family. The species "*arabica*" was named after the geographical region where it was first described. This taxon is native to the temperate-Asia zone. It covers the Fertile Crescent Mountains, Turkey, Iran and Iraq. In the Middle East it can be found in Lebanon, Syria, Israel (Judean Desert) and Jordans. *P. arabica* can be found in altitudes between 150-1,200 m and rarely up to 2,700 m. It is a bush, rather than a tree, with a very long root system and is considered resistant to drought[9,10]. As a deciduous tree, *P. arabica* drops its leaves at the end of the summer, turns meristems into buds and stops growing. However, unlike other almond species, young branches remain green and are not covered with bark (i.e., no cork layer deposition) throughout the dormancy phase (FIGS. 1A-D). In fact, *P. arabica* stems remain moist and green during the whole year. Although this phenomenon was described by researches who hypothesized those green stems to photosynthesize[11], up until now, no physiological evidence was published regarding the photosynthetic activity of the green stems of *P. arabica*, nor their ability to assimilate external $CO_2$ and their capability to transpire and respire.

Stem photosynthesis was previously shown in other desert species[12]. In these species, which do not belong to the Rosacea family, high efficiency of $CO_2$ assimilation comparable with that of the leaf was demonstrated[13]. The contribution of stem photosynthesis to tree adaptation under drought was further supported by evidence showing that stem photosynthesis assists in embolism repair[14,15].

Previous genetic studies of *P. arabica* were limited to phylogenetic studies and encompass a small number of markers (few to dozens)[17,18]. No genetic information is available to decipher the mechanism of the stem photosynthesis phenomena, despite availability of some genetic information [*P. dulcis* cv. Texas www(dot)ncbi(dot)nlm(dot)nih(dot)gov/bioproject/572860) and (www(dot)ncbi(dot)nlm(dot)nih(dot)gov/bioproject/553424)].

AGL82 is a DNA-binding transcription factor activity that modulates the transcription of specific gene sets transcribed by RNA polymerase II. To date there is no reported activity for this enzyme in fruit trees.

SUMMARY OF THE INVENTION

According to an aspect of some embodiments of the present invention there is provided a method of increasing yield of a domesticated *Prunus dulcis* plant, the method comprising:

(a) providing a progeny of a cross between a domesticated *Prunus dulcis* plant and a donor *Prunus amygdalus* plant comprising at least one sequence variation as described in Table 4 or at least one sequence variation in a gene as described in Table 5, wherein the at least one sequence variation is associated with stem photosynthetic capacity (SPC);

(b) identifying in the progeny a progeny plant exhibiting homozygosity to the at least one sequence variation, the progeny plant being characterized by increased yield as compared to the domesticated plant being nil or heterozygous to the at least one sequence variation.

According to an aspect of some embodiments of the present invention there is provided a method of increasing stem photosynthetic capability (SPC) in a domesticated *Prunus dulcis* plant, the method comprising:

(a) providing a progeny of a cross between a domesticated *Prunus dulcis* plant with a donor *Prunus amygdalus* plant characterized by stem photosynthetic capability (SPC); and (b) selecting a progeny plant exhibiting the SPC.

According to an aspect of some embodiments of the present invention there is provided a method of identifying a donor plant for use in a breeding program of *Prunus dulcis*, the method comprising identifying in a *Prunus amygdalus* plant a trait selected from the group consisting of stem photosynthetic capability (SPC) and a genome comprising at least one sequence variation as described in Table 4 or at least one sequence variation in a gene as described in Table 5.

According to some embodiments of the invention, the donor is wild *Prunus amygdalus.*

According to some embodiments of the invention, the wild *Prunus amygdalus* is *Prunus arabica* (Olivier) Meikle.

According to some embodiments of the invention, the at least one sequence variation is on chromosome 7 and/or chromosome 1.

According to some embodiments of the invention, the progeny plant is characterized by all year round enhanced $CO_2$ assimilation as compared to the domesticated *Prunus dulcis* plant.

According to some embodiments of the invention, the at least one sequence variation is selected from the group consisting of single nucleotide polymorphism (SNP) and a simple sequence repeat (SSR).

According to some embodiments of the invention, the domesticated *Prunus dulcis* plant is an *Prunus dulcis* cv. Um el Fachem (U.E.F.).

According to some embodiments of the invention, the gene is AGL82.

According to some embodiments of the invention, the sequence variation is a deletion.

According to some embodiments of the invention, the sequence variation is as set forth in SEQ ID NO: 1 or 2.

According to some embodiments of the invention, the identifying is by a method selected from the group consisting of allele-specific hybridization, Southern blot analysis, Northern blot analysis, in situ hybridization, deep-sequencing and polymerase chain reaction (PCR).

According to some embodiments of the invention, the method comprises:

(c) backcrossing the progeny of step (b) to produce backcross progeny plants;

(d) selecting a backcross progeny plant comprising the sequence variation, the progeny plant being characterized by SPC and increased yield as compared to the domesticated plant being nil or heterozygous to the at least one sequence variation.

According to some embodiments of the invention, the method comprises repeating steps (C) and (d) at least two times.

According to an aspect of some embodiments of the present invention there is provided a method of increasing yield of a domesticated *Prunus* (*dulcis* plant, the method comprising genetically modifying the plant to down-regulate activity and/or expression of AGL82, thereby increasing yield of a domesticated *Prunus dulcis* plant.

According to some embodiments of the invention, the genetically modifying is by genome editing.

According to some embodiments of the invention, the genetically modifying is by RNA silencing.

According to an aspect of some embodiments of the present invention there is provided a domesticated *Prunus dulcis* plant characterized by stem photosynthetic capability (SPC) and comprising in a genomic DNA thereof a nucleic acid variation which causes the SPC.

According to some embodiments of the invention, the nucleic acid variation is in AGL82.

According to an aspect of some embodiments of the present invention there is provided a seed of the plant as described herein.

According to an aspect of some embodiments of the present invention there is provided a method of producing a processed product of *Prunus dulcis*, the method comprising processing the seed as described herein.

According to an aspect of some embodiments of the present invention there is provided a processed product of the plant as described herein and comprising the genomic DNA.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F shows gas exchange measurements of *P. arabica* and *Prunus dulcis* cv. Um el Fachem (U.E.F.) stems. Three-year-old trees of the Israeli cultivar *Prunus dulcis* cv. U.E.F. (A), and the wild almond *P. arabica* (B) at spring. Stems of U.E.F. (C), and *P. arabica* (D) annually developed: one-year old (c1, d1), second year (c2, d2) and three years old stems (c3, d3). Gas exchange data of one-year old stems along the year (E) of *P. arabica* (solid gray line), and U.E.F. (dashed black line). Each dot denotes the average of two independent days of measuring for each month (n=8). Stem respiration rate in response to three different temperatures (F) of *P. arabica* (grey bar) and U.E.F. (black bar). Four stems were measured for each genotype in each temperature (n=4). Different capital letter represents significance ($\alpha$=0.05) between temperatures, not between species. The error bars represent ±SE.

FIGS. 2A-D show stem photosynthetic capability (SPC) in the F1 progeny. Levels of net $CO_2$ assimilation for each offspring (A). Each box plot presents the average of four stems (n=4). The F1 progeny parents, *P. arabica* and U.E.F. are marked by dashed arrow and simple arrow, respectively. Distribution histogram of the same data is presented in (B), while parents' data is highlighted. Measurements were conducted during February 2020 while the trees were dormant. Representative pictures of the F1 population while dormant (C) in February, and during the vegetative phase in April (D).

Figure 3:
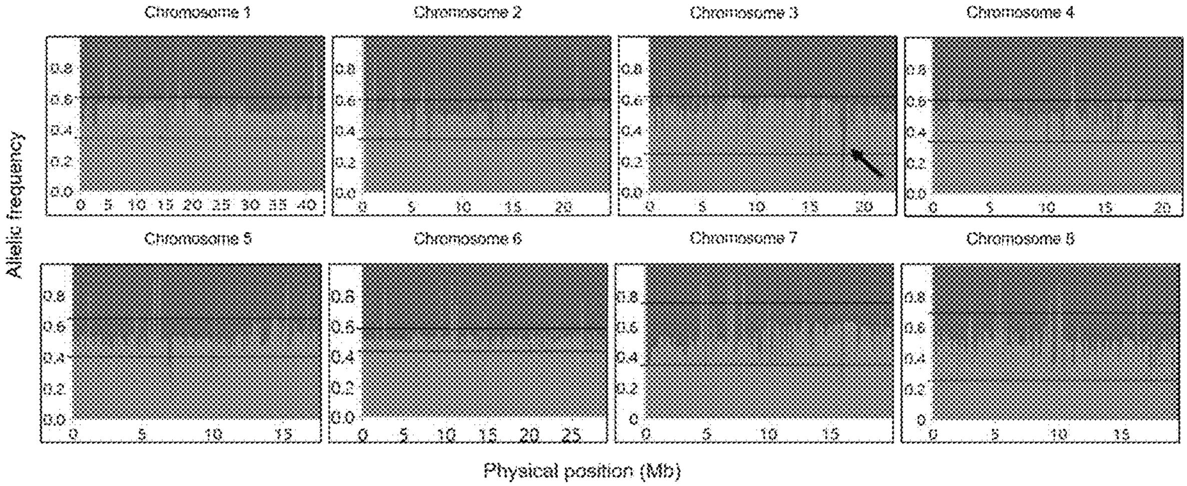

FIG. 3 shows allelic frequency among the F1 population. Allelic frequency of the heterozygous allele in the F1 population for each marker. Blue line indicates the *P. arabica* allelic incidence, and red line indicates the U.E.F. allelic incidence. X axis is the physical position in Mb, and Y axis represents the allelic ratio (from 0 to 1). Black arrow in chromosome 3 represents an example of un-expected deviated region ("hot spot"). References lines presented the 'tolerance interval' limits.

Figure 4:
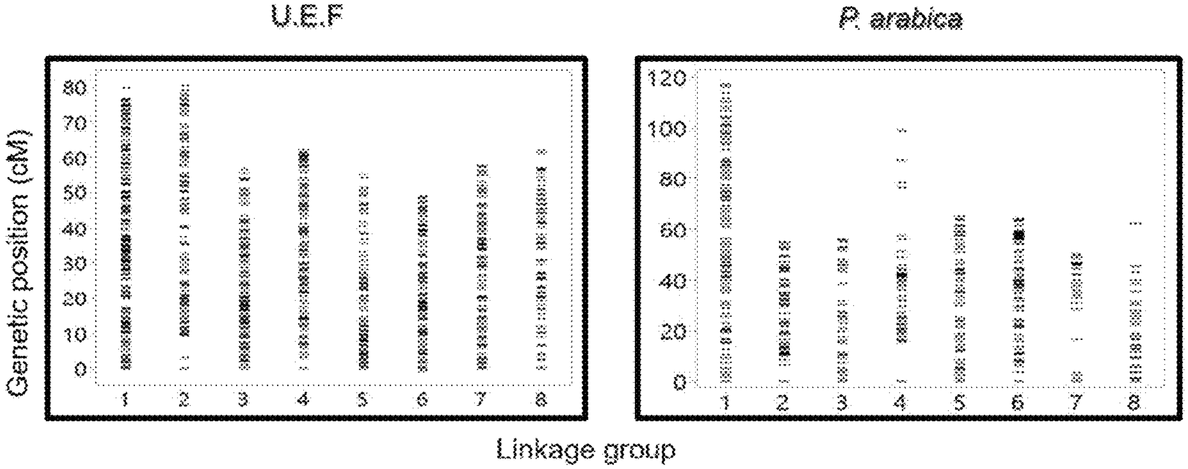

FIG. 4 shows graphic presentation of markers density and distribution along the eight linkage groups. Comparison between U.E.F. map (left graph) and *P. arabica* map (right graph). Each horizontal line represents a single marker.

Figure 5:
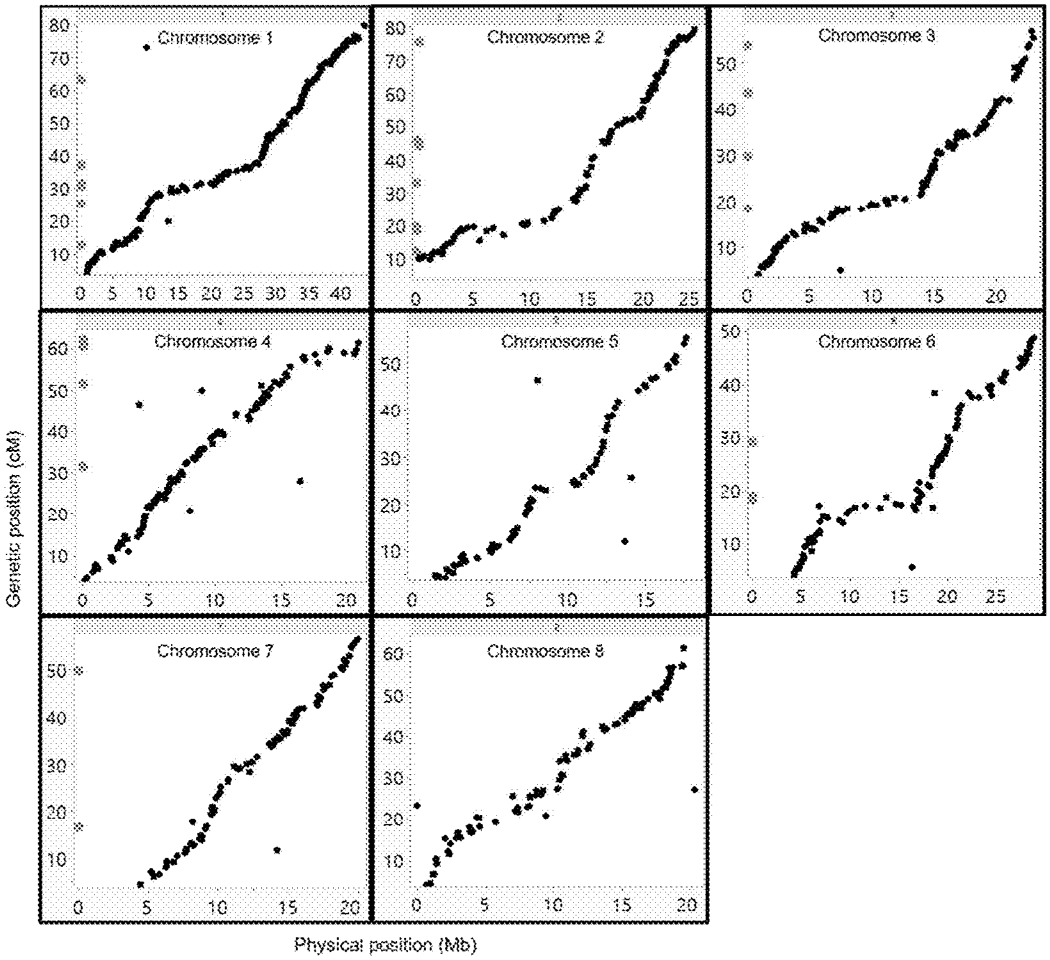

FIG. 5 shows a comparison between the genetic and physical order of the markers. SNP markers were placed according to their physical position on the Lauranne reference genome sequence (X axis) and their position on the U.E.F. genetic map (Y axes). The yellow dots represent markers from unplaced scaffolds, according to the Lauranne reference genome (chr-0). Those markers were mapped to chromosomes in this study based on the genetic map data.

FIGS. 6A-C show QTLs and GWAS analysis for the SPC trait. Major QTL of 2.4 Cm width and LOD score of 20.8, was located in chromosome 7 by using the U.E.F. genetic map (A). Minor QTL of 4.4 Cm width, and LOD score (3.9) was located at the end of chromosome 1 by using the *P. arabica* genetic map (B). Results of GWAS using the whole set of markers (3,800) sorted by their physical position according to the reference genome (C), revealed both loci in chromosome 7 and chromosome 1. Markers in c were sorted by their physical position according to the reference genome. Markers that were placed on chromosome 0 and found as highly associated to the SPC trait are also shown in (V). The horizontal dash line represents significance level according to permutation test (1000 times at $\alpha$=0.05).

FIGS. 7A-C show QTLs effect on net $CO_2$ assimilation and the synergistic effect between QTLs. Least square of means for each allelic combination is presented (A). Each box plot represents the population individuals average phenotype-grouped for their allelic combination. Y axis is the level of net $CO_2$ assimilation. The X axis represents the allelic combination. On the X axis, the capital letter A, refers to individuals with *P. arabica* allele combination, U refers to individuals with U.E.F. allele combination in each one of the QTL, and superscript numbers (7, 1) present the QTL identity. Numerical presentation of the data is presented in A (B). *P. arabica* allele combination is marked in green, and U.E.F. marker combination is marked in red. Different letters indicate significance ($\alpha$=0.05). Statistical evaluation of each QTL effect, and interaction between the two loci (C). Presented results were analyzed by the "Full factorial test", blue line is equivalent for p-value of $\alpha$=0.01.

FIGS. 8A-B show a schematic illustration of AGL82 in U.E.F, and 2 alleles of *Prunus arabica*, with the respective SEQ ID NOs: 6, 5 and 4 shown.

FIGS. 9A-B shows the F1 population is according to the allelic combination in the major QTL of locus 7, A for *P. arabica* parent and U for the U.E.F. Total yield was measured for each tree in the progeny (n=70) during July 2021. Asterisk meaning significance difference (A). Also presented is the LS mean of each group (B). Significant tested by the "Pooled t-test" $\alpha$=0.05.

DESCRIPTION OF SPECIFIC EMBODIMENTS OF THE INVENTION

The present invention, in some embodiments thereof, relates to methods of increasing yield of *Prunus dulcis* and plants produced thereby.

Almond (*Prunus dulcis* (Mill.) D. A. Webb) is a species of tree native to Iran and surrounding countries but widely cultivated elsewhere. In 2019, world production of almonds was 3.5 million tons, led by the United States, providing 55% of the world total. Other leading producers were Spain, Iran, and Turkey.

Almond production in California is concentrated mainly in the Central Valley, where the mild climate, rich soil, abundant sunshine and water supply make for ideal growing conditions. Due to the persistent droughts in California in the early 21$^{st}$ century, it became more difficult to raise almonds in a sustainable manner. In fact, climatic changes world-wide render profitable almond production more challenging.

Whilst conceiving embodiments of the invention, the present inventors uncovered the underlying mechanism of the stem photosynthetic capacity (SPC) of wild almond and harnessed it towards increasing $CO_2$ assimilation by the domesticated cultivar, thereby increasing its yield. Increase in $CO_2$ assimilation will compensate for the carbohydrate deficiency which happens during dormancy.

More specifically, *Prunus arabica* (Olivier) Meikle is a bushy wild almond species known for its green, un-barked stem, which stays green even during the dormancy period. The present study revealed that *P. arabica* green stems assimilate significantly high rates of $CO_2$ during the winter as compared to *P. dulcis* cv. Um el Fahem (U.E.F), thereby improving carbohydrate status throughout dormancy. To uncover the genetic inheritance and mechanism behind the *P. arabica* Stem Photosynthetic Capability (SPC), a segregated F1 population was generated by crossing *P. arabica* to U.E.F. Both parents' whole genome was sequenced, and a single nucleotide polymorphism (SNP) calling identified 4,887 informative SNPs for genotyping. A robust genetic map for U.E.F. and *P. arabica* was constructed (971 and 571 markers, respectively). QTL mapping and association study for the SPC phenotype revealed major QTL (log of odd (LOD)=20.8) on chromosome 7, and another minor but significant QTL on chromosome 1 (LOD=3.9). A list of sequence variations associated with the SPC trait as well as associated genes was generated.

These can be used in marker-assisted breeding for increasing the yield of domesticated almond.

Thus, according to an aspect of the invention, there is provided a method of identifying a donor plant for use in a breeding program of *P. dulcis*, the method comprising identifying in a *Prunus amygdalus* plant a trait selected from the group consisting of stem photosynthetic capability (SPC) and a genome comprising at least one sequence variation as described in Table 4 or at least one sequence variation in a gene as described in Table 5.

Identification of said trait is indicative of a plant suitable for use as a donor in a breeding program of *Prunus amygdalus.*

Wild or cultivated almond will be referred to herein as "*Prunus amygdalus*" or "*P. amygdalus*"

As used herein "*Prunus dulcis*" is also known as "*Prunus dulcis* (Mill.) D. A. Web". The terms are interchangeably used herein.

Other botanical names include: *Amygdalus communis* L.; *Prunus amygdalus* Bartock; *Prunus communis* (L.) Arcang. UPOV Name: PRUNU_DUL.

The term refers to the plant of the following classification:

Family: Rosaceae
Species: *P. dulcis*
Kingdom: Plantae
Subgenus: *Prunus* subg. *Amygdalus*
Order: Rosales Generally, the domesticated almond or cultivated almond is referred to herein as "domesticated *Prunus dulcis* species" and refers to a cultivated variety which is endowed with edible kernel or a seedling that originated from a cross between cultivated varieties.

According to a specific embodiment, the domesticated plant is a breeding line or clone.

According to a specific embodiment the plant line is an elite line.

Numerous domesticated lines of *Prunus dulcis* are known to date and expected to be available in the future.

A non-limiting list of almond cultivars which can be used as the domesticated recipient include, those listed in www (dot)fao(dot)org/3/x5337e/x5337e05(dot)htm, but are not limited thereto.

According to a specific embodiment, the domesticated *Prunus dulcis* is *Prunus dulcis* cv. Um el Fachem (U.E.F.).

According to a specific embodiment, the domesticated *Prunus dulcis* is *Prunus dulcis* cv. Matan.

According to a specific embodiment, the domesticated *Prunus dulcis* is *Prunus dulcis* cv. Laurrane According to a specific embodiment, the domesticated *Prunus dulcis* is *Prunus dulcis* cv. Shefa (Al. 54)

As used herein "a donor plant" refers to the parent from which sequences e.g., one or a few genes, also referred to an introgression, also referred to as sequence variation, are transferred to a recipient parent in a breeding program.

As used herein "introgression" or "introgressive hybridization" is the incorporation (usually via hybridization and backcrossing) of novel genes and/or alleles from one taxon into the gene pool of a second, distinct taxon. In this case from a donor parent, e.g., wild *Prunus amygdalus* to a recipient parent e.g., domesticated *P. dulcis*. This introgression is considered 'adaptive' if the genetic transfer results in an overall increase in the recipient taxon's fitness, in this case SPC and yield.

As used herein "recipient parent" typically refers to the domesticated variety which is either nil or heterozygous for the nucleic acid variation.

According to some embodiments the donor plant is wild *Prunus amygdalus.*

A wild almond species refers to any *Prunus amygdalus* which is not recognized as *dulcis* (e.g. *Prunus webbii, Prunus arabica* etc.). Wild almond can be defined as such only if it is not a product of some selection or an offspring of a cultivated almond. Wild almond is also characterized by its bitter kernel, smaller leaves and a bushier habit of growth than cultivated almond.

Examples of wild almond species include but are not limited to:

*Prunus Arabica;*
*Prunus scoparia* (Spach) C. K. Schneid; *Prunus spinosissima* (Bunge) Franch;
*Prunus webbii* (Spach) Vierh;
*Prunus ramonensis* Danin;
*Prunus tenella* (syn. Nana) Batsch;
*Prunus fenzliana* Fritsch.

According to a specific embodiment, the wild *Prunus* species (syn. *Amygdalus*) is *Prunus arabica* (Olivier) Meikle.

As used herein, the term "plant" refers to an entire plant, its organs (i.e., leaves, stems, roots, flowers etc.), seeds, plant cells, and progeny of the same. The term "plant cell" includes without limitation cells within seeds, suspension cultures, embryos, meristematic regions, callus tissue, leaves, shoots, gametophytes, sporophytes, pollen, and microspores.

The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like. According to a specific embodiment, the plant part comprises the nucleic acid variation as described herein. According to a specific embodiment, the plant part is a seed, which in almond is also the part of the highest commercial value.

As used herein "at least one sequence variation" refers to a genetic marker i.e., sequence data, which can be used to predict a plant characterized by SPC, without having it grown to the stage of stem production.

As used herein "predicting" refers to identification in advance of a trait in a plant before the plant exhibits a phenotype of the trait, e,g., SPC.

Methods of detecting sequence variations are well known in the art and are further described hereinbelow and in the Examples section which follows.

As used herein "stem photosynthetic capability (SPC)" refers to the ability of a stem of the plant to assimilate external $CO_2$ as demonstrated by its green color. Methods of determining parameters of plant physiology such as $CO_2$ assimilation or transpiration, which are physiologically linked are well known in the art, examples of which are provided in the Examples section which follows.

Due to lower surface area of stems relative to leaves, SPC is beneficial in harsh habitat. By maintaining transpiration, nutrients uptake and carbon gain during the winter, when leaves are not present, those essential processes can occur without loosing too much water. Moreover SPC provides sugar products and energy which are essential to prevent embolism. Lastly, extra energy in the form of sugars is essential to support leaf, flower and fruit development when the tree is breaking dormancy and energy storage is exhausted. This is particularly important in hot winters when respiration is much more substantial. Another important advantage of SPC is the reduced need to fertilize the soil with fertilizers, especially during winter time.

Thus, the present teachings provide for a method of increasing the ability to provide the cultivated almond trees with essential nutrients during dormancy when the plant sheds its leaves. Normally, when there are no leaves there is no transpiration and the plant cannot upload nutrients from soil. When the SPC trait is introduced as described above and below it is anticipated that such trees will be able to uptake nutrients. Nutrient uptake in winter could enhance yield and extend life expectancy of the trees.

As used herein "enhancing" or "increasing" refers to an increase of at least 10%, 20%, 30%, 40%, 50%, 60%, 70%, 80%, 90%, 1.5 fold, 2 fold or more as compared to a control of the same genetic background without the sequence variation (i.e., control plant e.g., the recipient plant).

As used herein "reducing" or "decreasing" refers to a decrease of at least 10%, 20%, 30%, 40%, 50%, 60%, 70%, 80%, 90%, 1.5 fold, 2 fold or more as compared to a control of the same genetic background without the sequence variation (i.e., e.g., the recipient plant).

As used herein the phrase "genetic marker" or "molecular marker" refers to a nucleic acid variation which is associated with SPC. The molecular marker can be at least one nucleic acid long or more such as a fragment of DNA that is associated with a certain location within the genome and with the trait.

Thus, the variation that may be of a single base, a few bases (2-10), or more (e,g., 11-100) bases to several hundreds e.g., 101-900 or thousands 1 Kb-1000 Kb or more of nucleotides confers the SPC.

The sequence variation may be selected from the group consisting of a substitution, an insertion, a deletion, a repeat, an inversion and a combination of same.

Methods of validating such variations and their association with the phenotype, in this case "SPC" are well known in the art and described in length in the Examples section which follows (see Examples 3-8).

As used herein "haplotype" refers to a combination of particular alleles present within a particular plant's genome at two or more linked marker loci, for instance at two or more loci on a particular linkage group.

The genetic marker may be in a coding sequence.

Examples of genes present in such coding sequences are provided in Table 5 below which is considered as an integral part of the specification.

According to a specific embodiment, the gene is "AGL82".

As used herein "AGL82" is the *Prunus dulcis* homolog of the gene AGL 82 of *Arabidopsis thaliana*. A member of the agamous-like (AGL) MADS box protein, which are known as a transcription factors involved in many physiological processes including organ development and identity and growth regulation. The AGL82 sequence is provided in the reference sequence of Um-el-Fachem (U.E.F) set forth in SEQ ID NO: 3. The sequence in the *Prunus arabica* (Olivier) plant is provided in SEQ ID NO: 1 or 2 (see also FIG. 8).

In one embodiment, the sequence variation is a deletion, as shown for instance in FIG. 8, in which the deletion is the coding sequence on the first AGL82 exon.

Alternatively or additionally, the genetic marker may be in a non-coding sequence.

According to a specific embodiment, the at least one genetic marker is a single nucleotide polymorphism (SNP) marker or an SSR. Using SSR the present inventors were able to show a 206 band in the domesticated varieties which are devoid of the variation while a 185 band was evident in the *P. arabica* cultivar.

According to a specific embodiment, the at least one genetic marker or markers is on chromosome 7, chromosome 1 or combination of same.

According to a specific embodiment, the at least one genetic marker or markers is on chromosome 7.

According to a specific embodiment, the at least one marker on chromosome 7 is positioned at genetic positions corresponding to those listed in Table 6 and detectable by the primer pair provided therein.

According to a specific embodiment, the at least one marker on chromosome 1 is positioned at genetic positions corresponding to those listed in Table 6 and detectable by the primer pair provided therein.

According to a specific embodiment, the genetic marker comprises at least one single nucleotide polymorphism (SNP) selected from the group of SNPs shown in Table 6 below.

According to a specific embodiment, the genetic marker comprises at least two single nucleotide polymorphisms (SNPs) selected from the group of SNPs shown in Table 6 below.

According to a specific embodiment, the genetic marker comprises at least three single nucleotide polymorphisms (SNPs) selected from the group of SNPs shown in Table 6 below.

According to a specific embodiment, the genetic marker comprises at least four single nucleotide polymorphisms (SNPs) selected from the group of SNPs shown in Table 6 below.

According to a specific embodiment, the genetic marker comprises at least five single nucleotide polymorphism (SNPs) selected from the group of SNPs shown in Table 6 below.

According to a specific embodiment, the genetic marker comprises at least six single nucleotide polymorphism (SNPs) selected from the group of SNPs shown in Table 6 below.

According to a specific embodiment, the genetic marker comprises at least seven single nucleotide polymorphism (SNPs) selected from the group of SNPs shown in Table 6 below.

According to a specific embodiment, the genetic marker comprises at least eight single or all nucleotide polymorphism (SNPs) selected from the group of SNPs shown in Table 6 below.

Molecular markers associated with the trait of interest may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet. 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis.

Thus, according to some embodiments, determining sequence variation comprises DNA sequencing of said at least one genetic marker.

According to some embodiments, determining sequence variation comprises amplifying said at least one genetic marker.

According to some embodiments, the at least one marker is detected by at least one primer pair or probe. Such primer pairs are provided in Table 6 below which should be considered as an integral part of the instant specification.

Thus, in some embodiments, the molecular markers or marker loci are detected using a suitable amplification-based detection method. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage and Caruthers (1981) Tetrahedron Letts 22:1859-1862, e.g., using a commercially available automated synthesizer, e.g., as described in Needham-VanDevanter, et al. (1984) Nucleic Acids Res. 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair or probe. For example, primers can be designed using any suitable software program, such as LASERGENE® or Primer3®.

According to some embodiments, the primer pair is selected from the list of Table 6 below which should be considered as an integral part of the instant specification.

It is not intended that the primers be limited to generating an amplicon of any particular size. For example, the primers used to amplify the marker loci and alleles herein are not limited to amplifying the entire region of the relevant locus. In some embodiments, marker amplification produces an amplicon at least 20 nucleotides in length, or alternatively, at least 50 nucleotides in length, or alternatively, at least 100 nucleotides in length, or alternatively, at least 200 nucleotides in length.

PCR, RT-PCR, and LCR are in particularly broad use as amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous references, such as Mullis, et al. (1987) U.S. Pat. No. 4,683,202; Arnheim & Levinson (1990) C&EN 36-47; Kwoh, et al. (1989) Proc. Natl. Acad. Sci. USA 86:1173; Guatelli, et al., (1990) Proc. Natl. Acad. Sci. USA 87:1874; Lomell, et al., (1989) J. Clin. Chem. 35:1826; Landegren, et al., (1988) Science 241:1077-1080; Van Brunt, (1990) Biotechnology 8:291-294; Wu and Wallace, (1989) Gene 4:560; Barringer, et al., (1990) Gene 89:117, and Sooknanan and Malek, (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype SNP alleles are provided. However, one of skill will immediately recognize that other primer and probe sequences could also be used. For instance primers to either side of the given primers can be used in place of the given primers, so long as the primers can amplify a region that includes the allele to be detected, as can primers and probes directed to other SNP marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain examples, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Strategies for labeling nucleic acids and corresponding detection strategies can be found, e.g., in Haugland (1996) Handbook of Fluorescent Probes and Research Chemicals Sixth Edition by Molecular Probes, Inc. (Eugene Oreg.); or Haugland (2001) Handbook of Fluorescent Probes and Research Chemicals Eighth Edition by Molecular Probes, Inc. (Eugene Oreg.).

Detectable labels may also include reporter-quencher pairs, such as are employed in Molecular Beacon and TaqMan™ probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent, depending on the embodiment. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, Handbook of Fluorescence Spectra of Aromatic Molecules, 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, Handbook of Fluorescent Probes and Research Chemicals, Molecular Probes of Eugene, Oreg., 1992, the content of which is incorporated herein by reference.

In certain examples, reporter-quencher pairs are selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other examples, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from Applied Biosystems, and the like. Suitable examples of quenchers may be selected from 6-carboxy-tetramethylrhodamine, 4-(4-dimethylaminophenylazo) benzoic acid (DABYL), tetramethylrhodamine (TAMRA), BHQ-O™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TaqMan™ probes. A molecular beacon (MB) is an oligonucleotide which, under appropriate hybridization conditions, self-hybridizes to form a stem and loop structure. The MB has a label and a quencher at the termini of the oligonucleotide; thus, under conditions that permit intramolecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone, et al. (1995) Nucl Acids Res. 26:2150-2155; Tyagi and Kramer (1996) Nat Biotechnol 14:303-308; Blok and Kramer (1997) Mol Cell Probes 11:187-194; Hsuih. et al. (1997) J Clin Microbiol 34:501-507; Kostrikis et al. (1998) Science 279:1228-1229; Sokol, et al. (1998) Proc. Natl. Acad. Sci. USA 95:11538-11543; Tyagi, et al. (1998) Nat Biotechnol 16:49-53; Bonnet, et al. (1999) Proc. Natl. Acad. Sci. USA 96:6171-6176; Fang, et al. (1999) J. Am. Chem. Soc. 121:2921-2922; Marras, et al. (1999) Genet. Anal. Biomol. Eng. 14:151-156; and Vet, et al. (1999) Proc. Natl. Acad. Sci. USA 96:6394-6399. Additional details regarding MB construction and use is found in the patent literature, e.g., U.S. Pat. Nos. 5,925,517; 6,150,097; and 6,037,130.

Another real-time detection method is the 5'-exonuclease detection method, also called the TaqMan™ assay, as set forth in U.S. Pat. Nos. 5,804,375; 5,538,848; 5,487,972; and 5,210,015, each of which is hereby incorporated by reference in its entirety. In the TaqMan™ assay, a modified probe, typically 10-25 nucleic acids in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook, et al., Molecular Cloning—A Laboratory Manual (3d ed.), Vol. 1-3, Cold Spring Harbor Laboratory, Cold Spring Harbor, N.Y., 2000 ("Sambrook"); Current Protocols in Molecular Biology, F. M. Ausubel, et al., eds., Current Protocols, a joint venture between Greene Publishing Associates, Inc. and John Wiley & Sons, Inc., (supplemented through 2002) ("Ausubel")) and PCR Protocols A Guide to Methods and Applications (Innis, et al., eds) Academic Press Inc. San Diego, Calif. (1990) (Innis). Additional details regarding detection of nucleic acids in plants can also be found, e.g., in Plant Molecular Biology (1993) Croy (ed.) BIOS Scientific Publishers, Inc.

Other techniques for detecting SNPs can also be employed, such as allele specific hybridization (ASH). ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Real-time amplification assays, including MB or TaqMan™ based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain examples, each allele-specific probe for a certain SNP locus is 11-20 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

To effectuate SNP allele detection, a real-time PCR reaction can be performed using primers that amplify the region including the SNP locus, for instance the sequences listed in Table 3, the reaction being performed in the presence of all allele-specific probes for the given SNP locus. By then detecting signal for each detectable label employed and determining which detectable label(s) demonstrated an increased signal, a determination can be made of which allele-specific probe(s) bound to the amplicon and, thus, which SNP allele(s) the amplicon possessed. For instance, when 6-FAM- and VIC-labeled probes are employed, the distinct emission wavelengths of 6-FAM (518 nm) and VIC (554 nm) can be captured. A sample that is homozygous for one allele will have fluorescence from only the respective 6-FAM or VIC fluorophore, while a sample that is heterozygous at the analyzed locus will have both 6-FAM and VIC fluorescence.

The KASPar® and Illumina® Detection Systems are additional examples of commercially-available marker detection systems. KASPar® is a homogeneous fluorescent genotyping system which utilizes allele specific hybridization and a unique form of allele specific PCR (primer extension) in order to identify genetic markers (e.g. a particular SNP locus associated with chloride salt stress tolerance). Illumina® detection systems utilize similar technology in a fixed platform format. The fixed platform utilizes a physical plate that can be created with up to 384 markers. The Illumina® system is created with a single set of markers that cannot be changed and utilizes dyes to indicate marker detection.

These systems and methods represent a wide variety of available detection methods which can be utilized to detect markers associated with SPC, but any other suitable method could also be used.

The molecular markers can be engaged in breeding methods by the use of what is commonly referred to as "marker assisted breeding (MAS)".

Thus, according to an aspect of the invention there is provided a method of increasing yield of a domesticated *Prunus dulcis* plant, the method comprising:

(a) providing a progeny of a cross between a domesticated *Prunus dulcis* plant and a donor *Prunus amygdalus* plant comprising at least one sequence variation as described in any one of Tables 1-6 or at least one sequence variation in a gene as described in FIG. 8, each of these tables are to be regarded as an integral part of the instant specification;

(b) identifying in said progeny a progeny plant exhibiting homozygosity to said at least one sequence variation, said progeny plant being characterized by increased yield as compared to the domesticated plant being nil or heterozygous to said at least one sequence variation.

It will be appreciated that the sequence variation above is associated with SPC according to a specific embodiment.

It will be further appreciated that according to a specific embodiment, the plant is homozygous for the sequence variation.

According to some embodiments, the domesticated *Prunus dulcis* plant (also referred to as a recipient plant or parent) is nil or heterozygous to the at least one sequence variation.

As used herein "yield" refers to weight of nuts (e.g., shelled nuts) per hectare in a growing season.

The average healthy and mature almond tree can produce 50-65 lbs. (23-30 kg) of nuts. A good yield of a mature commercial orchard run by professional almond growers is about 4500 lbs. (2040 kg) of shelled nuts per hectare.

As used herein, the term "progeny plant" or "progeny" refers to any plant resulting as progeny from a sexual reproduction between parent plants as described herein (cross) or descendants of the plant.

The progeny can be an F1, F2 and so on or backcross e.g., BCF1, BCF2 etc.

"Marker assisted selection" refers to the process of selecting a desired trait or traits in a plant or plants by detecting one or more nucleic acids from the plant, where the nucleic acid is associated with or linked to the desired trait, and then selecting the plant or germplasm possessing those one or more nucleic acids.

Hence the methods as described herein make use of MAS in some embodiments thereof.

Using MAS, plants or germplasm can be selected for markers that positively correlate with SPC, without actually raising the plant and measuring for the SPC (or, contrawise, plants can be selected against if they possess markers that negatively correlate with the trait i.e., SPC). MAS is a powerful tool to select for desired phenotypes and for introgressing desired traits into cultivars of *Prunus dulcis* (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

Thus, according to an aspect of the invention there is provided a method of breeding *Prunus dulcis*, the method comprising:

providing a cross between a first *Prunus amygdalus* parent plant and a second parent *Prunus dulcis* plant;

predicting SPC in said cross according to the teachings disclosed herein;

selecting a plant from said cross comprising the at least one genetic marker associated with tolerance to the SPC.

According to another aspect, there is provided a method of breeding *Prunus dulcis*, the method comprising:

predicting a SPC in *Prunus amygdalus* plants according to the teachings disclosed herein;

selecting at least one parent from the *Prunus amygdalus* plants comprising the at least one genetic marker associated with SPC; and crossing said at least one parent with a second *Prunus dulcis* plant.

According to another aspect, there is provided a method of *Prunus dulcis* growth, the method comprising:

predicting a SPC phenotype according to the teachings disclosed herein; and growing a plant comprising the at least one genetic marker associated with tolerance to the SPC.

Thus, one application of the tolerance markers is to increase the efficiency of an introgression or backcrossing effort aimed at introducing a tolerance trait into a desired (typically high yielding) background. In marker assisted backcrossing of specific markers from a donor source, e.g., to an elite genetic background, one selects among backcross progeny for the donor trait and then uses repeated backcrossing to the elite line to reconstitute as much of the elite background's genome as possible.

Thus, the markers and methods can be utilized to guide marker assisted selection or breeding of *Prunus dulcis* varieties with the desired complement (set) of allelic forms of chromosome segments associated with superior agronomic performance (such as yield but not limited thereto). Any of the disclosed markers or marker profiles can be introduced into a desired line via introgression, by traditional breeding (or introduced via transformation, or both) to yield a plant with superior agronomic performance.

In an alternative or additional aspect, the selection is phenotypic.

Thus, there is provided a method of increasing stem photosynthetic capability (SPC) in a domesticated *Prunus dulcis* plant, the method comprising:

(a) providing a progeny of a cross between a domesticated *Prunus dulcis* plant with a donor *Prunus amygdalus* plant characterized by stem photosynthetic capability (SPC); and (b) selecting a progeny plant exhibiting said SPC.

As mentioned according to some embodiments, increasing SPC can be done using genetic manipulation such as by down-regulating activity or expression of AGL82.

Thus, according to an aspect of the invention there is provided a method of increasing yield of a domesticated *Prunus dulcis* plant, the method comprising genetically modifying the plant to down-regulate activity and/or expression of AGL82, thereby increasing yield of a domesticated *Prunus dulcis* plant.

By doing so one can mimic the genetics and phenotype of *Prunus arabica* for example as shown in FIG. 8.

As used herein the phrase "downregulates expression" refers to downregulating the expression of a protein (e.g. AGL82) at the genomic (e.g. homologous recombination and site specific endonucleases) and/or the transcript level using a variety of molecules which interfere with transcription and/or translation (e.g., RNA silencing agents) or on the protein level (e.g., aptamers, small molecules and inhibitory peptides, antagonists, enzymes that cleave the polypeptide, antibodies and the like). It will be appreciated that although down regulation is described at length with respect to Agl82, other genes of Table 5 can be down regulated individually or in combination using the same methodology to achieve the envisaged phenotypes.

Down regulation of expression may be either transient or permanent.

According to specific embodiments, down regulating expression refers to the absence of mRNA and/or protein, as detected by RT-PCR or Western blot, respectively.

According to other specific embodiments down regulating expression refers to a decrease in the level of mRNA and/or protein, as detected by RT-PCR or Western blot, respectively. The reduction may be by at least a 10%, at least 20%, at least 30%, at least 40%, at least 50%, at least 60%, at least 70%, at least 80%, at least 90%, at least 95% or at least 99% reduction.

Non-limiting examples of agents capable of down regulating AGL82 expression are described in details hereinbelow.

Down-Regulation at the Nucleic Acid Level

Down-regulation at the nucleic acid level is typically effected using a nucleic acid agent, having a nucleic acid backbone, DNA, RNA, mimetics thereof or a combination of same. The nucleic acid agent may be encoded from a DNA molecule or provided to the cell per se.

According to specific embodiments, the downregulating agent is a polynucleotide.

According to specific embodiments, the downregulating agent is a polynucleotide capable of hybridizing to a gene or mRNA encoding AGL82.

According to specific embodiments, the downregulating agent directly interacts with agl82.

According to specific embodiments, the agent directly binds AGL82.

According to specific embodiments the downregulating agent is an RNA silencing agent or a genome editing agent.

Thus, downregulation of AGL82 can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs.

In one embodiment, the RNA silencing agent is capable of inducing RNA interference.

In another embodiment, the RNA silencing agent is capable of mediating translational repression.

According to an embodiment of the invention, the RNA silencing agent is specific to the target RNA (e.g., AGL82) and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

RNA interference refers to the process of sequence-specific post-transcriptional gene silencing in animals mediated by short interfering RNAs (siRNAs).

Following is a detailed description on RNA silencing agents that can be used according to specific embodiments of the present invention.

DsRNA, siRNA and shRNA—The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

According to some embodiments of the invention, dsRNA is provided in cells where the interferon pathway is not activated, see for example Billy et al., PNAS 2001, Vol 98, pages 14428-14433. and Diallo et al, Oligonucleotides, Oct. 1, 2003, 13(5): 381-392. doi:10.1089/154545703322617069.

According to an embodiment of the invention, the long dsRNA are specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term “siRNA” refers to small inhibitory RNA duplexes (generally between 18-30 base pairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is suggested to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned, the RNA silencing agent of some embodiments of the invention may also be a short hairpin RNA (shRNA).

The term “shRNA”, as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the AGL82 or another gene as contemplated herein mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, suitable siRNAs directed against one of the genes within the specified QTL region.

It will be appreciated that, and as mentioned hereinabove, the RNA silencing agent of some embodiments of the invention need not be limited to those molecules containing only RNA, but further encompasses chemically-modified nucleotides and non-nucleotides.

Downregulation of AGL82 can also be achieved by inactivating the gene (e.g., CRISPR/CAS9) via introducing targeted mutations involving loss-of function alterations (e.g. point mutations, deletions and insertions) in the gene structure.

As used herein, the phrase "loss-of-function alterations" refers to any mutation in the DNA sequence of a gene (e.g., AGL82) which results in downregulation of the expression level and/or activity of the expressed product, i.e., the mRNA transcript and/or the translated protein. Non-limiting examples of such loss-of-function alterations include a missense mutation, i.e., a mutation which changes an amino acid residue in the protein with another amino acid residue and thereby abolishes the enzymatic activity of the protein; a nonsense mutation, i.e., a mutation which introduces a stop codon in a protein, e.g., an early stop codon which results in a shorter protein devoid of the enzymatic activity; a frame-shift mutation, i.e., a mutation, usually, deletion or insertion of nucleic acid(s) which changes the reading frame of the protein, and may result in an early termination by introducing a stop codon into a reading frame (e.g., a truncated protein, devoid of the enzymatic activity), or in a longer amino acid sequence (e.g., a readthrough protein) which affects the secondary or tertiary structure of the protein and results in a non-functional protein, devoid of the enzymatic activity of the non-mutated polypeptide; a readthrough mutation due to a frame-shift mutation or a modified stop codon mutation (i.e., when the stop codon is mutated into an amino acid codon), with an abolished enzymatic activity; a promoter mutation, i.e., a mutation in a promoter sequence, usually 5' to the transcription start site of a gene, which results in down-regulation of a specific gene product; a regulatory mutation, i.e., a mutation in a region upstream or downstream, or within a gene, which affects the expression of the gene product; a deletion mutation, i.e., a mutation which deletes coding nucleic acids in a gene sequence and which may result in a frame-shift mutation or an in-frame mutation (within the coding sequence, deletion of one or more amino acid codons); an insertion mutation, i.e., a mutation which inserts coding or non-coding nucleic acids into a gene sequence, and which may result in a frame-shift mutation or an in-frame insertion of one or more amino acid codons; an inversion, i.e., a mutation which results in an inverted coding or non-coding sequence; a splice mutation i.e., a mutation which results in abnormal splicing or poor splicing; and a duplication mutation, i.e., a mutation which results in a duplicated coding or non-coding sequence, which can be in-frame or can cause a frame-shift.

According to specific embodiments loss-of-function alteration of a gene may comprise at least one allele of the gene.

The term "allele" as used herein, refers to any of one or more alternative forms of a gene locus, all of which alleles relate to a trait or characteristic. In a diploid cell or organism, the two alleles of a given gene occupy corresponding loci on a pair of homologous chromosomes.

According to other specific embodiments loss-of-function alteration of a gene comprises both alleles of the gene. In such instances the e.g. AGL82 may be in a homozygous form or in a heterozygous form. According to this embodiment, homozygosity is a condition where both alleles at the e.g. AGL82 locus are characterized by the same nucleotide sequence. Heterozygosity refers to different conditions of the gene at the e.g. AGL82 locus.

Methods of introducing nucleic acid alterations to a gene of interest are well known in the art [see for example Menke D. Genesis (2013) 51: -618; Capecchi, Science (1989) 244:1288-1292; Santiago et al. Proc Natl Acad Sci USA (2008) 105:5809-5814; International Patent Application Nos. WO 2014085593, WO 2009071334 and WO 2011146121; U.S. Pat. Nos. 8,771,945, 8,586,526, 6,774,279 and UP Patent Application Publication Nos. 20030232410, 20050026157, US20060014264; the contents of which are incorporated by reference in their entireties] and include targeted homologous recombination, site specific recombinases, PB transposases and genome editing by engineered nucleases. Agents for introducing nucleic acid alterations to a gene of interest can be designed publically available sources or obtained commercially from Transposagen, Addgene and Sangamo Biosciences.

Following is a description of various exemplary methods used to introduce nucleic acid alterations to a gene of interest and agents for implementing same that can be used according to specific embodiments of the present invention.

Genome Editing using engineered endonucleases—this approach refers to a reverse genetics method using artificially engineered nucleases to cut and create specific double-stranded breaks at a desired location(s) in the genome, which are then repaired by cellular endogenous processes such as, homology directed repair (HDR) and non-homologous end-joining (NFfEJ). NFfEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity. Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8, 163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is Fokl. Additionally Fokl has the advantage of requiring dimerization to have nuclease activity and this means the specificity increases dramatically as each nuclease partner recognizes a unique DNA sequence. To enhance this effect, Fokl nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the nonhomologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010).

In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

CRISPR-Cas system—Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRISPR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

Non-limiting examples of a gRNA that can be used in the present invention include those which target to exon 1 of ag182 gene.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type. The end result is the introduction of the desired modification without the retention of any exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats. Cre recombines the 34 base pair lox DNA sequence by binding to the 13 base pair inverted repeats and catalyzing strand cleavage and relegation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvk and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. Dec. 1, (2003) 31(23): 6873-6881]. Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred. The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified. Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors which enable insertion, deletion or substitution of DNA sequences in the genomes of live mammalian cells. The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Regardless the method of production, the present teachings provide for a domesticated *Prunus dulcis* plant characterized by stem photosynthetic capability (SPC) and comprising in a genomic DNA thereof a nucleic acid variation which causes said SPC.

According to a specific embodiment the nucleic acid variation is in AGL82.

According to a specific embodiment the plant is a plant part being a seed (i.e., nut, e.g., shelled).

Also provided are processed almond products which are produced from the plants described herein and preferably contain the nucleic acid sequence conferring the improved yield as described herein. Also provided are methods of processing the almond (e.g., to produce meal or other processed products).

Almond products are used in the food and non-food industry.

Almond products are used as meal, crushed, slices, intact salted, unsalted, fresh, frozen, milk, animal food produced from shells, etc.

In the non-food industry they are used in hygiene (e.g., shampoos, soaps, conditioners), cosmetics and enzyme industry.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Plant Material

All trees are growing in the almond orchard in Newe Ya'ar Research Center in the Yizre'el Valley (latitude 34042'N, longitude 35011'E, Mediterranean temperate to subtropical climate). The parents of the F1 population, *P. arabica* and the Israeli leading commercial cv. Um el Fahem (U.E.F) are grown at two copies for each, grafted on GF.677 rootstock, and planted in winter 2018. The F1 population (*P. arabica* X U.E.F) contains 92 seedlings that were germinated in the nursery in winter 2017 and replanted in the orchard in winter 2018.

Gas Exchange Measurements

Gas exchange measurements were done in the field on one-year old stems (i.e. current year growth) of three years old *P. arabica* and *P. dulcis* (U.E.F) trees, from October 2019 to October 2020. Each month, two reciprocal days were chosen; in each day, four stems per genotype were analyzed (n=8 per month). All measurements were conducted between the hours 8:30-10:30 a.m. (the latest were in winter). When there were leaves on the stems, they were removed two days prior to measurements to eliminate wounding stress effect. Measurements were carried out with the LI-6800 Portable Photosynthesis System (LI-COR Biosciences, USA), using the 6×6-needle chamber, which is compatible with tree branches of 2.5-4.5 mm diameter. The following conditions were held constant in the chamber:

photon flux density of 1,200 μmol m-2 sec-1 (90% red, 10% blue) and $CO_2$ reference of 400 PPM was set. Chamber relative humidity, and the temperature held for each month according to the multi-annual average. Gas exchange results were normalized to stem surface area and displayed as net assimilation rates (mol $CO_2$ $m^{-2}$ $sec^{-1}$), transpiration rates (mmol $H_2O$ $m^{-2}$ $sec^{-1}$), and instantaneous water use efficiency (iWUE; the ratio between net assimilation and transpiration rates).

Gas exchange measurements on the F1 population were conducted in February 2020 for two weeks, while the trees were dormant, between the hours 9:30-11:30 a.m. Four stems were measured (n=4) for each genotype. The measurement protocol was the same as mentioned above. To determine stem respiration rates, stem gas exchange measurements were conducted under the same conditions as described above. Next, the Licor 6800 light source was turned off for ~2 minutes (for stabilization of $\Delta CO_2$), and data were recorded. In dark, the net assimilation value represents respiration. Stem respiration rate was recorded under 17° C., 28° C. and 34° C.

Whole Genome Sequencing (WGS) and SNP Calling

DNA extracted from young leaves using the plant/fungi DNA isolation kit (NORGEN BIOTEK CORP, Canada). DNA of *P. arabica* and U.E.F, was sent to Macrogen (Macrogen, Korea) for WGS—Illumina Nova Seq 6000, with targeted coverage of X50 on average, read length of 150 bp with paired-end sequencing. OmicsBox software (version 1.3.11; www(dot)biobam(dot)com/omicsbox/) was used for preprocessing the raw-reads based on Trimmomatic40 for removing adapters and contamination sequences, trimming low-quality bases, and filtering short and low-quality reads. The cleaned reads were mapped onto the reference genomes: *P. dulcis* cv. Lauranne: (www(dot)ncbi(dot)nlm(dot)nih(dot)gov/bioproject/ 553424) and *P. dulcis* cv. Texas (www(dot)ncbi(dot)nlm (dot)nih(dot)gov/bioproject/572860), using the Burrows-Wheeler Aligner (BWA) software 0.7.12-r1039, with its default parameters41. The resulting mapping files were processed using SAMtools/Picard tool (broadinstitute(dot) github(dot)io/picard/, version 1.78)42; for adding read group information, sorting, marking duplicates, and indexing. Then, the local realignment process for locally realigning reads was performed so that the number of mismatching bases was minimized across all reads using the RealignerTargetCreator and IndelRealigner of the Genome Analysis Toolkit version 3.4-0 (GATK; version www(dot)broadinstitute(dot)org/gatk/)43. Finally, the variant calling procedure was performed using HaplotypeCaller of the GATK toolkit (gatk(dot)broadinstitute(dot)org/hc/en-us) developed by Broad Institute of MIT and Harvard (Cambridge, MA, USA). Only sites with DP (read depth) higher than 20 were further analyzed. SnpEff program44 was used to categorize the effects of the variants in the genomes (Table 1). The program annotates the variants based on their genomic location (intron, exon, untranslated region, upstream, downstream, splice site, or intergenic regions) including in the Almond GFF file extracted from the NCBI database (GCA_008632915.2). Then it predicts the coding effect such as synonymous or non-synonymous substitution, start or stop codon gains or losses, or frame shifts.

Population Genotyping

Based on WGS of *P. arabica* and U.E.F, a SNP calling was performed in order to select SNPs that will detect polymorphism within the F1 population. The following criteria were set: (1) remove sites with DP lower than 20; (2) an isolated SNP over 100 bp interval; (3) the SNP is unique with no matching on other genomic regions on the reference genome; (4) informative SNPs for the F1 population, that are homozygous for one parent and heterozygous for the other. In addition, SNPs were chosen at intervals of 40 kb along the almond genome (*P. dulcis* cv. Lauranne; www(dot)ncbi(dot) nlm(dot)nih(dot)gov/bioproject/553424) to obtain an unbiased representation through the whole chromosomes. Overall, a set of 5,000 markers was selected for genotyping (FIG. 3). The F1 population screening was accomplished by "targeted SNP Seq" by LGC (LGC Genomics, Germany) for SNPs genotyping.

Genetic Map Construction

For generating the genetic map the JoinMap®4.1 software25 was used. Cross-pollination population type was used with the code lmxll for markers that were homozygous for the male parents (*P. arabica*) and heterozygous in the female parent (U.E.F), and the code nnxnp for the opposite case. Because there were no common markers (hkxhk) we did not combine the two marker types, and undertook the pseudo test cross method, meaning we separated the markers into two different maps, one map for the U.E.F. (where *P. arabica* is homozygous-lmxll code), and one for the *P. arabica* parent (where U.E.F. is homozygous nnxnp code). Markers were filtered for three parameters: (1) More than ~11% missing data; (2) Non-Mendelian segregation (X2>6.5, DF=1) (3) Remove markers in similarity of 1.0. The "Independence LOD" algorithm was used for linkage groups clustering (LOD>8), and the Kosambi's function was chosen for calculating genetic distance.

QTL Mapping

In order to conduct the QTL analysis we used the Map QTL®5 software26. QTLs and their significance were calculated using interval mapping (IM). A QTL was determined as significant when its LOD score was higher than the calculated threshold (1000 permutation at $\alpha$=0.05), and the QTL spanning was determined by ±1 LOD from the max LOD marker.

Genome Wide Association Study (GWAS)

Association was calculated by TASSEL 5.2.5927. The set of SNPs was filtered; marker discard when missing data was >8.6%, and the allele frequency was set for 0.2<x<0.8 for preventing overestimated impact of rare alleles. The General linear model (GLM) was applied for the phenotypic and genotypic intersect data set to test the association. Threshold for significance result was assessed by 1000 permutation test $\alpha$=0.05.

Statistics

All significance tests were done by the statistical software JMP (JMP® PRO 15.0.0 © 2019 SAS Institute Inc.), $\alpha$=0.05. To test significance when the variance was unequal, a simple T-test was used, and if it was equal, the pooled t-Anova test was performed. Tukey-Kremer's test was used to analyze variance in the population when the distribution was normal, and the variance inside the groups was equal; when it was not equal or normal, Wilcoxon non-parametric test was used. Broad sense heritability of the SPC was calculated on the F1 (full sibs) by the 'Rsquare adj' value, given by a simple Anova test.

Example 1

*P. arabica* Assimilate $CO_2$ Through Green Stems

*P. arabica* stems remain green during winter while cultivated almonds develop an outer grey cork layer (FIGS. 1B and D). To study if these stems are actively assimilating $CO_2$, gas exchange measurements of tree stems in the orchard were undertaken with the Licor 6800 Portable Photosynthesis System. Two different almond species were compared, the wild almond *P. arabica* and the cultivated almond *P. dulcis* (U.E.F), throughout the entire year (FIG. 1E). The data indicate that *P. arabica* assimilates $CO_2$ through its green stems during all year (annual average of 8±0.19 mol $CO_2$ $m^{-2}$ $sec^{-1}$), while similar one-year old stems of U.E.F. assimilation capacity is almost nil (annual average of 0.5±0.05 mol $CO_2$ $m^{-2}$ $sec^{-1}$). The significantly high $CO_2$ assimilation rates of *P. arabica* stems were found comparable with assimilation rates of *P. arabica* leaves (11.2±0.8 $CO_2$ $m^{-2}$ $sec^{-1}$, July average, data not shown). Moreover, although some fluctuations were observed between the different seasons, pronounced high $CO_2$ assimilation rates were found in *P. arabica* stem during the whole year (FIG. 1E). Finally, *P. arabica* stem transpiration rate is relatively low in the dormancy phase and gradually increases until it peaks in October (1.2±0.18 in January to 5±0.7 mmol H2O $m^{-2}$ $sec^{-1}$ in October). In contrast, transpiration from U.E.F. stems is relatively constant and low throughout the year (0.46±0.11 mmol $H_2O$ $m^{-2}$ $sec^{-1}$; FIG. 1E). Transpiration rate fluctuation also attribute to high instantaneous water use efficiency (iWUE) of *P. arabica* during the dormancy phase (two-fold higher than U.E.F. in December; FIG. 1E).

To find out how stem respiration of *P. arabica* and U.E.F. are influenced by temperature, the respiration rate of one-year old stems was measured while exposing them to three different temperatures (17°, 28° and 34° C.) (FIG. 1F). Increased respiration rate in response to elevated temperature was observed in both almond species (0.5±0.11, 2.2±0.27, 3.5±0.44 and 0.33±0.12, 1.4±0.35, 3±0.68 mol $CO_2$ $m^{-2}$ $sec^{-1}$ for *P. arabica* and U.E.F. respectively for each temperature), while no significant differences were observed between species (for each measured temperature).

Example 2

Stem Assimilation is Genetically Inherited

Figure 2:
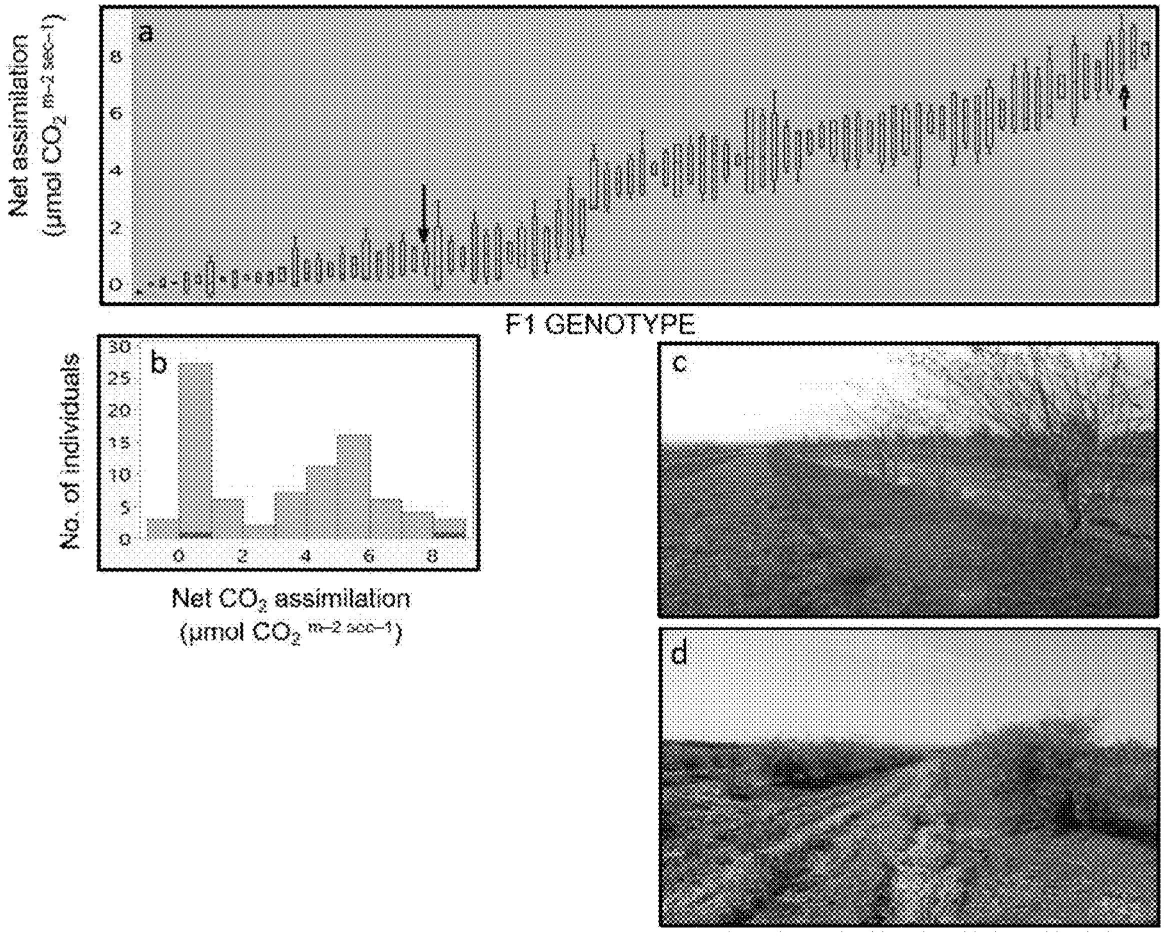

To elucidate the genetic nature of the assimilating stem trait of *P. arabica*, an F1 hybrid population (n=92) was established by crossing *P. arabica* (male) with U.E.F. (female) (FIGS. 2C-D). The same approach of gas exchange measurements in the field was used for phenotyping the SPC trait among the three year-old F1 population during dormancy. Twelve offspring assimilated $CO_2$ via their stems in a similar level as *P. arabica* (offspring 24H27 is the highest; 8.3±0.14 mol $CO_2$ $m^{-2}$ $sec^{-1}$), and Thirty-seven individuals assimilated as U.E.F. or less (FIG. 2A). Analysis of distribution demonstrated two prominent peaks within the histogram (FIG. 2B). Although the '3 Normal Mixture' is the most accurate to describe the phenotype distribution (achieved the lowest AICc and the −2 Log Likelihood values), broad-sense heritability ($h^2$) was found to be high (0.91).

Example 3

Sequence Comparisons, SNPs Identification, and Genotyping of the F1 Population Segregation of the SPC trait among the F1 population rendered it as suitable for genetic mapping. For this purpose, the *P. arabica* and the U.E.F. genomic DNA were sequenced, targeting for high coverage, to ensure reliable (SNP) calling. The reads were aligned against the reference genome of *P. dulcis* cv. Lauranne, which was found as the closest (>97% mapped reads) of the two published almond genomes (Table 1). A total of U.S. Pat. Nos. 3,750,363 and 2,407,787 variants (i.e., SNPs or short InDels) were detected for *P. arabica* and U.E.F. respectively, against the cv. Lauranne reference genome. Analyzing the variants showed that 71.5% and 72.6% (*P. arabica* and U.E.F, respectively) are in the intergenic region (Table 1). Furthermore, a higher variant number was detected in the intronic regions in relation to the exons (Table 1). The initial number of identified SNPs (Total variant sites in Table 2) were filtered by several types of criteria as specified in materials and methods.

Overall, 4,887 SNPs that are heterozygous for one of the parents and homozygous for the second were selected for F1 genotyping screening. The SNPs are spread at intervals of about 40K along the almond genome.

The F1 population was successfully genotyped with 4,6125 SNPs. The resulting genotyping quality data (Table 3) represent high coverage (152×), and low number of missing data (5.5%). Further analysis of the genotyped F1 population with the SNP panel described above show the allelic frequency within the F1 population is 50%, as expected from an F1 population (FIG. 3). However, since the allelic composition in this bi-parental population is AA×Aa, this ratio can also be referred to as the allelic frequency of the heterozygous genotype. Therefore, data presented (FIG. 3) also indicates exceptional chromosomal regions (hot spot) with a unique pattern of inheritance that deviates from the 1:1 ratio, for example, in chromosome 3 (see black arrow in FIG. 3).

Example 4

Construction of Genetic Maps for the F1 Population

To establish a genetic map of the F1 population, Join Map 4.1 software was used[25]. CP (cross pollination) population type was performed with the lmxll code for markers that were homozygous for the male parents (*P. arabica*) and heterozygous for the female parent (U.E.F). The code nnxnp used for the opposite case. A significant portion of the markers was filtered, most of them due to complete similarity (~50%). Overall, 1,533 SNPs were used for mapping (Table 2). Because there were no common markers for both parents, the hkxhk code was not applied. Using the pseudo test cross method[21], the markers were separated for two different maps: one map for the U.E.F. (where *P. arabica* is homozygous, lmxll code), and the second map for the *P. arabica* parent (where U.E.F. is homozygous, nnxnp code). Applying this strategy, two maps were obtained with robust numbers of markers and good density. The U.E.F. map was found to be denser than the *P. arabica* map and includes 971 markers with an average distance of 0.533 centiMorgen (cM), while *P. arabica* map contains 572 SNPs with an average distance of 1.093 (cM) (Table 2). It can be clearly seen that the distribution of the SNP markers is well spread over the eight almond linkage groups (LG) (FIG. 4).

To assess the validity of the genetic map, the order of SNP markers as determined by the U.E.F. genetic map was compared with the deduced order from the physical map as determined by cv. Lauranne reference genome. The analysis (FIG. 5) demonstrates a good co-linearity between the genetic and the physical map. Remarkably, most of the markers from the genetic map were highly correlated with the physical order (FIG. 5), yet, few markers did not correlate (chromosome 6, FIG. 5). The genetic map divided the markers into eight LGs parallel to the previously published chromosome organization order. Moreover, the slopes generated between the physical orders to the genetic order represent recombination frequency (cM/Mb). Thus, one can see that around the centromere, the slope is more horizontally, meaning the cM/Mb ratio is relatively low. Thirty-eight SNP markers representing un-scaffold contigs (i.e., chromosome 0) in the reference genome project were assembled into six linkage groups based on the genetic maps (marked by yellow dots in FIG. 5).

Example 5

QTL Analysis and Genome Wide Association Study (GWAS) of the SPC Trait

Two main approaches were initiated for detecting genomic regions regulating the SPC. QTL mapping, computed with Map QTL by interval mapping (IM) analysis[26] and Genome wide association (GWAS) by TASSEL software. QTL mapping generated two significant QTLs. Each QTL was discovered only in one of the two genetic maps. Thus, one major QTL (LOD=20.8) was mapped on LG 7 spanning a region of 2.4 cM detected on the U.E.F. map. The second, minor but significant QTL (LOD=3.9) was detected at the end LG 1, spanning a region of 4.4 cM on the *P. arabica* map (Table 4, FIG. 6 A-C). Applying GWAS approach with TASSEL enabled to simultaneously detect two genomic sites that regulate the SPC on chromosomes 1 and 7 at positions similar to those detected by QTL mapping. The major region on chromosome 7 spanning only 400 kb, and the minor on chromosome 1 containing 700 kb. Moreover, GWAS analysis showed significant associations with markers aligned to chromosome 0. Interestingly, two of these markers assembled into the major QTL in locus 7 (Table 4, marked with gray background). The major QTL explained 67% of the phenotypic variance, while the minor QTL explained 19.3% (Table 4).

Example 6

QTL's Interaction

As presented, two significant loci were discovered as regulating the SPC (FIG. 6A-C, Table 4). Full factorial test shows a significant additive effect between those two associated loci (<0.0001; FIGS. 7A-B). Yet, no epistatic effect was found (p-value=0.676; FIG. 7C). As expected, in both QTLs the *P. arabica* alleles were the increasing alleles regarding the SPC trait.

Example 7

Generating a List of Candidate Genes

Combining GWAS and QTLs data described above with that of the cv. Lauranne reference sequence allowed delineating a list of genes within the regions that are predicted as responsible for the SPC trait. The region at chromosome 1 includes 113 annotated genes with SNPs between *P. arabica* and U.E.F. (Table 5). Among those, 17 include non-synonymous SNPs in the genes coding region. The associated region at chromosome 7 consists 336 genes with SNPs, of which only 54 have non-synonymous SNPs in their coding region (Table 5).

Example 8

AGL 82 Protein Modification

FIG. 8 compares between *P. arabica* and U.E.F. genomic sequences around the deletion (FIG. 8*a*). Also provided an exon-intron scheme (FIG. 8*b*) presenting the first allele of *P. arabica* with 21 bp deletion—no frameshift observed when comparing to the wild type (U.E.F). Nonetheless, in *P. arabica* second allele which presents a deletion of only 17 bp, a frameshift occurred resulting in a much shorter exon (marked in black).

Example 9

QTL Effect on Almond Fruit Yield

Stem photosynthesis during dormancy should provide extra carbon gain for the deciduous almond. This energy source may be expressed in higher productivity. FIG. 9A-B divides the F1 population to individuals with the *P. arabica* allele (A) in the major QTL (locus 7) or with the U.E.F. allele (U). Significantly higher yield was observed in the individuals presenting the A allele.

TABLE 1

Variant's effect. Summarized variant's (SNPs and InDels) effect comparing between *P. arabica* and U.E.F. All data shown analyzed by the SnpEff program (SnpEff 5.0d version). Only SNPs with DP >20 were analyzed.

| | | | | | | Variant region | | | Exon variant effect | |
|---|---|---|---|---|---|---|---|---|---|---|
| Species | Total variant | Variant rate | Hetero-zygous | Homo-zygous | Hetero-zygosity (%) | Intergenic | Intron | Exon | Non-synonymous | Synon-ymous |
| *P. arabica* | 3,750,363 | 1/53 bp | 2,431,092 | 1,319,271 | 35.18 | 2,679,858 | 534,963 | 201,677 | 106,017 | 78,054 |
| U.E.F | 2,407,787 | 1/83 bp | 739,341 | 1,668,446 | 69.29 | 1,748,138 | 322,135 | 122,631 | 63,323 | 43,718 |

TABLE 2

Quality data from whole genome sequencing of *P. arabica* and U.E.F. Quality parameters (Q20, Q30) from sequencing of each parent is presented with respect to the reference genomes of *P. dulcis* cv. Lauranne and *P. dulcis* cv. Texas. The row sequence data was mapped to each of the reference genomes. The total variant sites (SNPs and InDels) between each species and cv. Lauranne reference genome are also presented.

| Species | Average coverage | Q20 | Q30 | % Mapping VS Lauranne | % Mapping VS Texas | Total variant sites | % Heterozygous variant sites |
|---|---|---|---|---|---|---|---|
| *P. arabica* | ~X 57 | 94.5 | 87.37 | 97.93 | 85.94 | 3,750,363 | 35.18 |
| U.E.F (*P.dulcis*) | ~X 55.5 | 94.7 | 87.71 | 98.37 | 89.82 | 2,407,787 | 69.29 |

TABLE 3

| Genotyping quality parameters for the selected SNPs. Genotyping results | |
|---|---|
| number of markers | 4887 |
| number of markers after quality filtering (>8 aligned read per snp's, and are polymorphic) | 4612 (94.4%) |
| average coverage per marker | 152X |
| homozygous sites | 68.70% |
| heterozygous sites | 31.30% |
| missing data | 5.50% |

Data provided by LGC Genomics (LGC Genomics, Germany).

TABLE 4

List of highly linked markers, found by GWAS and QTL mapping, regulating the SPC trait. Markers highly associated with the QTLs are presented according to their method of detection. Grey markers represent markers from chr-0 which were found by the genetic map on chr-7. The QTL boundaries defined by ±1 LOD or by the significance threshold. Marker ID also represents its physical position.

| Method of mapping | | LG | genetic position (cM) | LOD | Variance | % Expl. | markers included |
|---|---|---|---|---|---|---|---|
| QTL mapping | U.E.F | 7 | 1.992 | 18.71 | 2.21994 | 64.6 | CHR-7_1438852 |
| | Map | 7 | 2.522 | 20.29 | 2.03376 | 67.6 | AP020412-1_49668 |
| | | 7 | 2.533 | 20.29 | 2.03376 | 67.6 | CHR-7_2892468 |
| | | 7 | 2.956 | 20.29 | 2.03376 | 67.6 | CHR-7_4162127 |
| | | 7 | 3.151 | 20.29 | 2.03376 | 67.6 | AP020714-1_7925 |
| | | 7 | 3.453 | 20.29 | 2.03376 | 67.6 | CHR-7_4198814 |
| | | 7 | 4.381 | 18.39 | 2.25941 | 64 | CHR-7_4461774 |
| | *P.* | 1 | 108.237 | 3.24 | 5.23604 | 16.5 | CHR-1_38279493 |
| | *arabica* | 1 | 109.237 | 3.62 | 5.09664 | 18.7 | |
| | Map | 1 | 110.237 | 3.83 | 5.06117 | 19.2 | |
| | | 1 | 110.514 | 3.87 | 5.05604 | 19.3 | CHR-1_38494350 |
| | | 1 | 110.514 | 3.87 | 5.05604 | 19.3 | CHR-1 38362855 |
| | | 1 | 111.514 | 3.43 | 5.1651 | 17.6 | |
| | | 1 | 111.647 | 3.32 | 5.21425 | 16.8 | CHR-1_38943531 |
| | | 1 | 112.647 | 3.05 | 5.2712 | 15.9 | |
| | | **Chromosome** | **physical position (bp)** | **LOD** | **Variance** | **% Expl.** | **Markers included** |
| Association mapping[b] | | 7 | 4,012,513 | 19.2 | 2.27476 | 64.581 | CHR-7_4012513 |
| | | 7 | 4,162,127 | 20.8 | 2.08398 | 64.581 | CHR-7_4162127 |
| | | 7 | 4,198,814 | 20.8 | 2.08398 | 64.581 | CHR-7_4198814 |
| | | 7 | 4,265,958 | 20.8 | 2.08398 | 64.581 | CHR-7_4265958 |
| | | 7 | 4,295,653 | 20.8 | 2.08398 | 64.581 | CHR-7_4295653 |
| | | 7 | 4,334,831 | 20.8 | 2.08398 | 64.581 | CHR-7_4334831 |
| | | 7 | 4,461,774 | 18.9 | 2.3152 | 64.581 | CHR-7_4461774 |
| | | 1 | 38,279,493 | 3.8 | 5.36532 | 16.46 | CHR-1_38279493 |
| | | 1 | 38,362,855 | 4.5 | 5.18088 | 16.46 | CHR-1_38362855 |
| | | 1 | 38,494,350 | 4.5 | 5.18088 | 16.46 | CHR-1_38494350 |
| | | 1 | 38,536,093 | 4.5 | 5.18088 | 16.46 | CHR-1_38536093 |
| | | 1 | 38,577,293 | 4.5 | 5.18088 | 16.46 | CHR-1_38577293 |
| | | 1 | 38,658,589 | 4.5 | 5.18088 | 16.46 | CHR-1_38658589 |
| | | 1 | 38,739,041 | 4.5 | 5.18088 | 16.46 | CHR-1_38739041 |
| | | 1 | 38,779,086 | 4.5 | 5.18088 | 16.46 | CHR-1_38779086 |
| | | 1 | 38,862,559 | 4.5 | 5.18088 | 16.46 | CHR-1_38862559 |
| | | 1 | 38,943,531 | 3.9 | 5.343 | 16.46 | CHR-1_38943531 |
| | | 1 | 38,985,216 | 3.9 | 5.343 | 16.46 | CHR-1_38985216 |
| | | 0 (scaff_x) | 9,272 | 20.8 | 2.08398 | 67.552 | AP020412-1_9272 |
| | | 0 (scaff_x) | 49,668 | 20.8 | 2.08398 | 67.552 | AP020412-1_49668 |
| | | 0 (scaff_x) | 94,298 | 20.8 | 2.08398 | 67.552 | AP020412-1_94298 |
| | | 0 (scaff_x) | 136,487 | 20.8 | 2.08398 | 67.552 | AP020412-1_136487 |
| | | 0 (scaff_y) | 38,995 | 20.8 | 2.08398 | 67.552 | AP020477-1_38995 |
| | | 0 (scaff_z) | 7,925 | 20.8 | 2.08398 | 67.552 | AP020714-1_7925 |

TABLE 5

| Candidate genes annotation list. | | | | |
|---|---|---|---|---|
| QTL | Gene ID | Chromosome | Position (bp) | Description |
| Locus 1 | Prudu_004391 | 1 | 38,301,438 | Protein phosphatase 2C family protein |
| | Prudu_004392 | 1 | 38,312,029 | alpha/beta-Hydrolases superfamily protein |
| | Prudu_004397 | 1 | 38,334,995 | Outer arm dynein light chain 1 protein |
| | Prudu_004400 | 1 | 38,361,883 | peptidases |
| | Prudu_004403 | 1 | 38,392,534 | UDP-glucosyl transferase 85A2 |
| | Prudu_004404 | 1 | 38,417,559 | UDP-glucosyl transferase 85A2 |
| | Prudu_004408 | 1 | 38,446,031 | UDP-glucosyl transferase 85A2 |
| | Prudu_004415 | 1 | 38,491,373 | Class-II DAHP synthetase family protein |
| | Prudu_004416 | 1 | 38,497,457 | transferases (transferring glycosyl groups) |
| | Prudu_004444 | 1 | 38,695,641 | Putative disease resistance TIR-NBS-LRR class protein |
| | Prudu_004452 | 1 | 38,778,771 | MATE efflux family protein |
| | Prudu_004456 | 1 | 38,826,980 | Pentatricopeptide repeat-containing protein |
| | Prudu_004457 | 1 | 38,829,424 | Tetratricopeptide repeat-like superfamily protein |
| | Prudu_004463 | 1 | 38,853,771 | Homeodomain-like transcriptional regulator |
| | Prudu_004471 | 1 | 38,902,580 | FH interacting protein 1 |
| | Prudu_004484 | 1 | 39,005,185 | phosphoglucose isomerase |
| | Prudu_004530 | 1 | 39,470,338 | binding |
| Locus 7 | Prudu_018743 | 7 | 1,441,299 | phosphatidylinositolglycan synthase family protein |
| | Prudu_018746 | 7 | 1,486,403 | BURP domain-containing protein |
| | Prudu_018760 | 7 | 1,640,243 | Leucine-rich repeat receptor-like protein kinase family protein |
| | Prudu_018765 | 7 | 1,691,276 | transposable element gene |
| | Prudu_018774 | 7 | 1,786,237 | zinc ion binding |
| | Prudu_018777 | 7 | 1,861,699 | Major facilitator superfamily protein |
| | Prudu_018778 | 7 | 1,873,924 | hypothetical protein |
| | Prudu_018781 | 7 | 1,908,274 | hypothetical protein |
| | Prudu_018795 | 7 | 2,075,667 | zinc ion binding |
| | Prudu_018806 | 7 | 2,198,976 | homolog of X-ray repair cross complementing 3 |
| | Prudu_018810 | 7 | 2,283,474 | small and basic intrinsic protein 2 |
| | Prudu_018815 | 7 | 2,359,300 | Restriction endonuclease 2C type II-like superfamily protein |
| | Prudu_018816 | 7 | 2,374,926 | SU(VAR)3-9 homolog |
| | Prudu_018817 | 7 | 2,387,985 | hypothetical |
| | Prudu_018820 | 7 | 2,470,388 | alpha-L-arabinofuranosidase 1 |
| | Prudu_018825 | 7 | 2,561,001 | transposable element gene |
| | Prudu_018832 | 7 | 2,656,886 | cysteine-rich RECEPTOR-like protein kinase 26 |
| | Prudu_018834 | 7 | 2,669,396 | hypothetical protein; protein |
| | Prudu_018857 | 7 | 2,972,898 | Subtilisin-like serine endopeptidase family protein |
| | Prudu_018862 | 7 | 3,041,435 | HXXXD-type acyl-transferase family protein |
| | Prudu_018869 | 7 | 3,151,517 | BED zinc finger |
| | Prudu_018881 | 7 | 3,413,913 | hypothetical protein |
| | Prudu_018882 | 7 | 3,424,410 | BURP domain-containing protein |
| | Prudu_018883 | 7 | 3,431,279 | EPIDERMAL PATTERNING FACTOR-like protein 2 |
| | Prudu_018891 | 7 | 3,465,742 | HAESA-like 2 |
| | Prudu_018895 | 7 | 3,511,841 | hexokinase-like 3 |
| | Prudu_018904 | 7 | 3,587,067 | UDP-glucosyltransferase 74F2 |
| | Prudu_018907 | 7 | 3,610,860 | UDP-Glycosyltransferase superfamily protein |
| | Prudu_018910 | 7 | 3,635,340 | phosphoenolpyruvate carboxykinase 1 |
| | Prudu_018912 | 7 | 3,663,238 | myb family transcription factor |
| | Prudu_018918 | 7 | 3,750,133 | Glycosyl hydrolase family protein |
| | Prudu_018922 | 7 | 3,774,085 | Protein of unknown function |
| | Prudu_018924 | 7 | 3,792,676 | Leucine-rich repeat protein kinase family protein |
| | Prudu_018929 | 7 | 3,849,642 | Concanavalin A-like lectin protein kinase family protein |
| | Prudu_018930 | 7 | 3,853,817 | Concanavalin A-like lectin protein kinase family protein |
| | Prudu_018931 | 7 | 3,863,434 | ABC-2 type transporter family protein |
| | Prudu_018934 | 7 | 3,899,076 | cinnamyl alcohol dehydrogenase 6 |

TABLE 5-continued

Candidate genes annotation list.

| QTL | Gene ID | Chromo-some | Position (bp) | Description |
|---|---|---|---|---|
| | Prudu_018936 | 7 | 3,937,669 | Homeodomain-like superfamily protein |
| | Prudu_018939 | 7 | 3,965,026 | hypothetical protein |
| | Prudu_018943 | 7 | 4,015,960 | UDP-glucose 6-dehydrogenase family protein |
| | Prudu_018951 | 7 | 4,070,501 | DNA/RNA helicase protein |
| | Prudu_018957 | 7 | 4,172,297 | lectin protein kinase family protein |
| | Prudu_018969 | 7 | 4,275,773 | MADS-box transcription factor family protein (AGL82) |
| | Prudu_018972 | 7 | 4,334,098 | hypothetical protein |
| | Prudu_018973 | 7 | 4,345,554 | microtubule-associated proteins 70-2 |
| | Prudu_018974 | 7 | 4,352,521 | disease resistance family protein/LRR family protein |
| | Prudu_018983 | 7 | 4,436,188 | hypothetical protein |
| | Prudu_018989 | 7 | 4,515,872 | hypothetical protein |
| | Prudu_018993 | 7 | 4,556,661 | Disease resistance protein TIR-NBS-LRR class family |
| | Prudu_018994 | 7 | 4,560,295 | Disease resistance protein TIR-NBS-LRR class family |
| | Prudu_018999 | 7 | 4,640,563 | multidrug resistance-associated protein |
| | Prudu_019014 | 7 | 4,799,013 | hypothetical protein |
| | Prudu_75S000300 | AP020412.1 | 59,974 | hypothetical protein |
| | Prudu_75S000800 | AP020412.1 | 87,203 | hypothetical protein |

Annotation of the genes beneath the two QTL's according to their physical position, after filtering for genes with only non-synonymous variant located in the coding region.

TABLE 6

Primers for the associated markers. Presented here the forward and the revers probes for amplifying the SNPs markers with their physical position on the reference almond genome.
A_SNP and U_SNP are from P. arabica allele (A) and the U.E.F. allele (U), respectively

| Chr | Start | Stop | Marker_ID | Oligo_Sequence/SEQ ID NO | Tm | A_SNP | U_SNP | REF_SNP |
|---|---|---|---|---|---|---|---|---|
| 1 | 38, 279, 437 | 38, 279, 477 | AP019297-1_38279493 | CAGTTGAAATGCCCGGTTTTGACAAATGCAGGAGCCTGAG/7 | 57.294 | GC | GG | G |
| 1 | 38, 279, 507 | 38, 279, 547 | AP019297-1_38279493 | AAGGTTTATGATGACTATATATTGAAAATTTGTTTACTTG/8 | 44.608 | | | |
| 1 | 38, 494, 305 | 38, 494, 345 | AP019297-1_38494350 | GTTCAACTGTTAGCTTTACTGTTCTCATGTTGTAGGTTTG/9 | 50.922 | CT | CC | C |
| 1 | 38, 494, 368 | 38, 494, 408 | AP019297-1_38494350 | CTGCAGTATAAAGAAACAAGTGACCAGCATATGATTTGAA/10 | 50.488 | | | |
| 1 | 38, 943, 483 | 38, 943, 523 | AP019297-1_38943531 | GTTCGCTTCTCCCAGATAAACCATCTGCCATCGTCACTTC/11 | 56.103 | GA | GG | G |
| 1 | 38, 943, 549 | 38, 943, 589 | AP019297-1_38943531 | TAACTATAAATATTTCGTGGTCATTTTCTTATCTGTGTTG/12 | 46.66 | | | |
| 7 | 2, 892, 415 | 2, 892, 455 | AP019303-1_2892468 | TTACAACCCTATAATGAAAGATATAATGATGGGTATAGTG/13 | 46.234 | TT | TC | T |
| 7 | 2, 892, 491 | 2, 892, 531 | AP019303-1_2892468 | CATGGTGGACATCCAAGGGGGAGTGTTGTAACTTTCAAGG/14 | 55.849 | | | |
| 7 | 4, 012, 453 | 4, 012, 493 | AP019303-1_4012513 | CTTGACATATGAAAATTTGTTGTTTATCTGTGCTAAGTTC/15 | 48.065 | CC | CT | C |
| 7 | 4, 012, 535 | 4, 012, 575 | AP019303-1_4012513 | ACAGATATTCTGTCCTTGCAACGTCTGCACACCAACAAGC/16 | 56.544 | | | |
| 7 | 4, 162, 069 | 4, 162, 109 | AP019303-1_4162127 | CCCAAGATTTGTACGTGATGCTTCAGTGCCAACTGATAAT/17 | 53.926 | GG | GT | G |
| 7 | 4, 162, 138 | 4, 162, 178 | AP019303-1_4162127 | AAGGGTAGCTAATTTGAAGAATGGGTCAATGAGCTGCCTA/18 | 53.765 | | | |
| 7 | 4, 461, 724 | 4, 461, 764 | AP019303-1_4461774 | CGAACAAGATACGGCATGACCACTGAAAAAGATTTGATTT/19 | 52.321 | CC | AC | A |
| 7 | 4, 461, 781 | 4, 461, 821 | AP019303-1_4461774 | CCTAAATAAAGGGGGAGAACAAGGATTTCTTGCTTTGATA/20 | 50.744 | | | |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of marker-assisted selection, the method comprising:

(a) providing progeny plants of a cross between a recipient domesticated *Prunus dulcis* plant having edible seed and a donor *Prunus arabica* plant, said donor *Prunus arabica* plant comprising at least one sequence variation in the AGAMOUS-like 82 (AGL82) gene, wherein said at least one sequence variation comprises SEQ ID NO: 2, wherein said at least one sequence variation is associated with stem photosynthetic capability (SPC), which is demonstrated by having a green stem during dormancy; and (b) subjecting said progeny plant to selfing or backcrossing to a recipient domesticated *Prunus dulcis* plant having edible seed, to produce descendant progeny plants, (c) identifying in the descendant progeny plants a progeny plant exhibiting homozygosity to said at least one sequence variation, said progeny plant being characterized by increased yield due to said SPC during dormancy, as compared to the recipient domesticated *Prunus dulcis* plant not having said at least one sequence variation or heterozygous for said at least one sequence variation and wherein said identifying is by a method selected from the group consisting of allele-specific hybridization, Southern blot analysis, Northern blot analysis, in situ hybridization, deep-sequencing and polymerase chain reaction (PCR).

2. The method of claim 1, wherein said donor *Prunus arabica* is *Prunus arabica* (Olivier) Meikle.

3. The method of claim 1, wherein said descendant progeny plant is characterized by all year-round enhanced $CO_2$ assimilation as compared to the domesticated *Prunus dulcis* plant.

4. The method of claim 1, wherein said domesticated *Prunus dulcis* plant is a *Prunus dulcis* cv. Um el Fachem (U.E.F.) plant.

* * * * *